(12) United States Patent
Vallier et al.

(10) Patent No.: US 10,000,740 B2
(45) Date of Patent: Jun. 19, 2018

(54) IN VITRO PRODUCTION OF FOREGUT STEM CELLS

(71) Applicant: Cambridge Enterprise Limited, Cambridge (GB)

(72) Inventors: Ludovic Vallier, Cambridge (GB); Nicholas Hannan, Cambridge (GB)

(73) Assignee: Cambridge Enterprise Limited (GB)

( * ) Notice: Subject to any disclaimer, the term of this patent is extended or adjusted under 35 U.S.C. 154(b) by 0 days. days.

(21) Appl. No.: 15/028,085

(22) PCT Filed: Oct. 6, 2014

(86) PCT No.: PCT/EP2014/071363
§ 371 (c)(1),
(2) Date: Apr. 8, 2016

(87) PCT Pub. No.: WO2015/052143
PCT Pub. Date: Apr. 16, 2015

(65) Prior Publication Data
US 2016/0237401 A1    Aug. 18, 2016

(30) Foreign Application Priority Data
Oct. 9, 2013    (GB) .................................. 1317869.4

(51) Int. Cl.
*C12N 5/071* (2010.01)
*G01N 33/50* (2006.01)

(52) U.S. Cl.
CPC ........... *C12N 5/068* (2013.01); *C12N 5/0672* (2013.01); *C12N 5/0678* (2013.01); *C12N 5/0689* (2013.01); *G01N 33/5023* (2013.01); *C12N 2500/92* (2013.01); *C12N 2501/11* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/385* (2013.01); *C12N 2501/40* (2013.01); *C12N 2501/415* (2013.01); *C12N 2501/91* (2013.01); *C12N 2501/999* (2013.01); *C12N 2506/02* (2013.01); *C12N 2506/45* (2013.01)

(58) Field of Classification Search
CPC .... C12N 5/0672; C12N 5/0678; C12N 5/068; C12N 2500/90; C12N 2501/16
See application file for complete search history.

(56) References Cited

U.S. PATENT DOCUMENTS

| | | | |
|---|---|---|---|
| 2006/0040387 A1 | 2/2006 | Fisk et al. | |
| 2009/0269845 A1* | 10/2009 | Rezania | C12N 5/0606 435/366 |
| 2010/0015711 A1* | 1/2010 | Davis | C12N 5/0678 435/377 |
| 2011/0091971 A1 | 4/2011 | Davis et al. | |

FOREIGN PATENT DOCUMENTS

| | | |
|---|---|---|
| EP | 2233566 A1 | 9/2010 |
| WO | 2009/027654 A1 | 3/2009 |
| WO | 2010/049752 A1 | 5/2010 |
| WO | 2010/091241 A2 | 8/2010 |
| WO | 2012/025725 A1 | 3/2012 |
| WO | 2012/170853 A1 | 12/2012 |
| WO | 2012/175633 A1 | 12/2012 |

OTHER PUBLICATIONS

Vallier et al, Stem Cells 27:2655-2666, 2009.*
Touboul et al, Hepatology 51:1754-1765, 2010.*
International Search Report issued from corresponding PCT/EP2014/071363, dated Jan. 9, 2015.
Kin Cheng et al: "Self-Renewing Endodermal Progenitor Lines Generated from Human Pluripotent Stem Cells", Cell Stem Cell, vol. 10, No. 4, Apr. 1, 2012 (Apr. 1, 2012), pp. 371-384, XP055131273, ISSN: 1934-5909, DOI: 10.1016/j.stem.2012.02.024.
Michael D Green et al: "Generation of anterior foregut endoderm from human embryonic and induced piuripotent stem cells", Nature Biotechnology, vol. 29, No. 3, Mar. 1, 2011 (Mar. 1, 2011), pp. 267-272, XP055070096, ISSN: 1087-0156, DOI: 10.1038/nbt.1788.
Nicholas R.F. Hannan et al: "Generation of Multipotent Foregut Stem Cells from Human Pluripotent Stem Cells", Stem Cell Reports, vol. 1, No. 4, Oct. 10, 2013 (Oct. 10, 2013), pp. 293-306, XP055159255, ISSN: 2213-6711, DOI:10.1016/J.stemcr.2013.09.003.
Song, Z. et al., Efficient generation of hepatocyte-like cells from human induced pluripotent stem cells, Cell Research, Nov. 2009; vol. 19, No. 11, pp. 1233-1242.
Vallier, L. et al., Signaling Pathways Controlling Pluripotency and Early Cell Fate Decisions of Human Induced Pluripotent Stem Cells, Stem Cells, 2009, vol. 27, pp. 2655-2666.
Vallier, L. et al., Early Cell Fate Decisions of Human Embryonic Stem Cells and Mouse Epiblast Stem Cells are Controlled by the Same Signalling Pathways,PLoS ONE, 2009, vol. 4, No. 6, e6082, pp. 1-13.
McClean, A. et al., Activin A Efficiently Specifies Definitive Endoderm from Human Embryonic Stem Cells Only When Phosphatidylinositol 3-Kinase Signaling is Suppressed, Stem Cells, 2007, vol. 25, pp. 29-38.
James, D. et al., TGFbeta/activin/nodal signaling is necessary for the maintenance of pluripotency in human embryonic stem cells, Development, 2005, vol. 132, pp. 1273-1282.

(Continued)

*Primary Examiner* — Kevin K Hill
(74) *Attorney, Agent, or Firm* — Banner & Witcoff, Ltd.

(57) ABSTRACT

This invention relates to the differentiation of pluripotent cells (PSCs) into foregut stem cells (FSCs) using a definitive endoderm induction medium comprising a TGFβ ligand, fibroblast growth factor (FGF), bone morphogenetic protein (BMP) and a PI3K inhibitor to differentiate the pluripotent cells into definitive endoderm cells and a foregut induction medium comprising a TGFβ ligand to differentiate the definitive endoderm cells into foregut stem cells (FSCs). Methods of differentiation, populations of foregut stem cells, culture media and kits are provided.

12 Claims, 15 Drawing Sheets

(56) References Cited

OTHER PUBLICATIONS

Hui, G. et al., Generation of murine hepatic lineage cells from induced pluripotent stem cells, Differentiation, 2010, vol. 79, pp. 171-181.

Xu, X. et al., Activin, BMP and FGF pathways cooperate to promote endoderm and pancreatic lineage cell lifferentiation from human embryonic stem cells, Mechanisms of Development, 2011, vol. 127, pp. 412-427.

Chng, Z. et al., Activin/Nodal Signaling and Pluripotency, Vitamins & Hormones, 2011, vol. 85, Chapter 3, pp. 39-58.

Lima, M. et al., Pancreatic Transcription Factors Containing Protein Transduction Domains Drive Mouse Embryonic Stem Cells towards Endocrine Pancreas, PlosOne, 2012, vol. 7, No. 5, pp. 1-10.

Touboul, T. et al., Generation of Functional Hepatocytes from Human Embryonic Stem Cells Under Chemically Defined Conditions that Recapitulate Liver Development, Hepatology, 2010, vol. 51, No. 5, pp. 1754-1765.

* cited by examiner

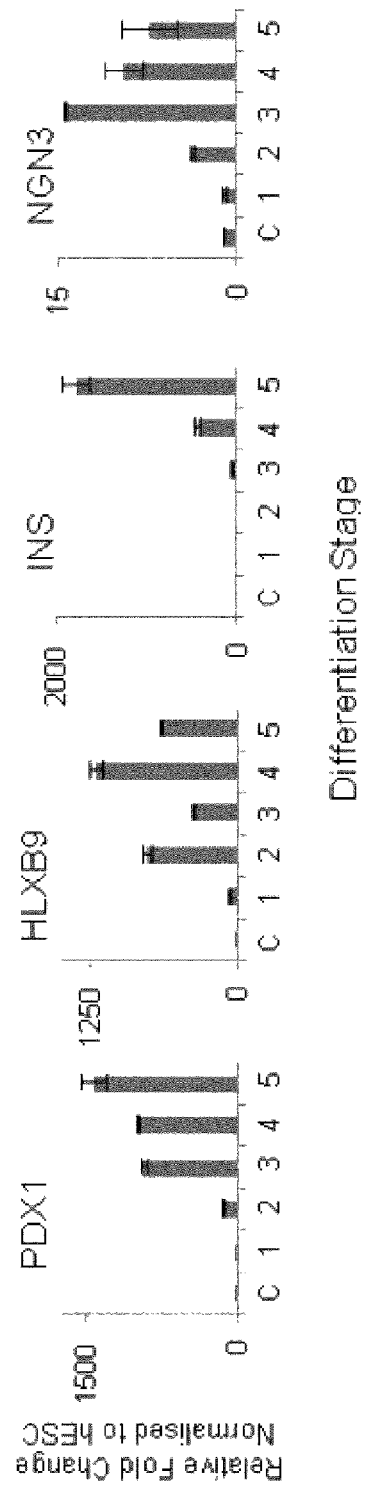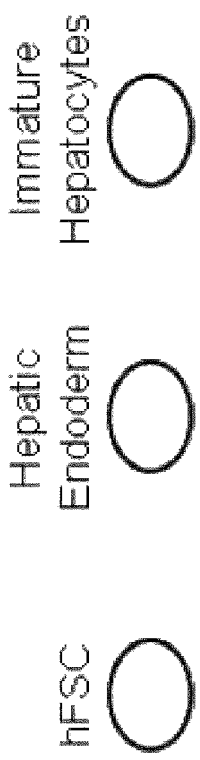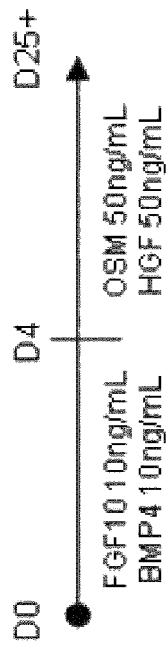
Figure 2F
Figure 2G

IN VITRO PRODUCTION OF FOREGUT STEM CELLS

RELATED APPLICATIONS

This application is a National Stage Application under 35 U.S.C. 371 of co-pending PCT application PCT/EP2014/071363 designating the United States and filed Oct. 6, 2014; which claims the benefit of GB application number 1317869.4 and filed Oct. 9, 2013 each of which are hereby incorporated by reference in their entireties.

FIELD

This invention relates to the in vitro production of foregut stem cells, for example for use in the production of cells of endodermal lineages.

BACKGROUND

The development of a universal protocol to differentiate any hPSC line into a homogenous population of a specific cell type has been rendered difficult by the inherent variability that exists between lines. Epigenetic memory, inconsistent reprogramming and genetic background are likely to be the main cause of this variability which represents a major challenge for the development of personalised medicines[1, 21] and for modelling diseases with a low penetrance phenotype. The expansion of intermediate stages of differentiation could represent an attractive alternative to address this issue, especially if these cell types can be isolated from a heterogeneous population. For example, Neuronal Stem Cells can be easily expanded from hIPSC lines differentiated toward the neuroectoderm lineage and then differentiated into a diversity of neurones thereby bypassing the need to continuously grow pluripotent cells [2]. However, the same approach with endoderm differentiation has been more problematic since the complex combination of inductive signals controlling the specification and patterning of this germ layer can be difficult to mimic in vitro[3].

SUMMARY

The present inventors have developed a defined culture system to derive human Foregut Stem Cell (hFSCs) from hPSCs. These stem cells can self-renew in vitro and resemble multipotent cells of the anterior primitive gut tube by their capacity to differentiate into pancreatic, hepatic and lung endoderm cells. Furthermore, hFSCs may be derived from hIPSC lines resistant to endoderm differentiation thereby enabling the production of endodermal derivatives from a broad number of hPSC lines. This may be useful in the in vitro production of endoderm cells for research and therapeutic applications.

An aspect of the invention provides a method for producing a population of foregut stem cells (FSCs), the method comprising:
  i) providing a population of pluripotent cells (PSCs),
  ii) culturing the PSCs in a definitive endoderm induction medium comprising a TGFβ ligand, fibroblast growth factor (FGF), bone morphogenetic protein (BMP) and a PI3K inhibitor to produce a first population of cells;
  iii) culturing the first population of cells in a foregut induction medium comprising a TGFβ ligand to produce a population of foregut stem cells (FSCs).

Another aspect of the invention provides a method for producing a population of foregut stem cells (FSCs), the method comprising:
  i) providing a population of definitive endoderm cells (DECs);
  ii) culturing the population of DECs in a foregut induction medium comprising a TGFβ ligand, preferably activin, to produce a population of foregut stem cells (FSCs).

The population of definitive endoderm cells (DECs) may be homogenous or heterogenous.

The population of FSCs may be cultured or passaged in an FSC maintenance medium comprising a TGFβ ligand, preferably activin, fibroblast growth factor (FGF), bone morphogenetic protein (BMP), HGF, EGF, and Heparin.

Another aspect of the invention provides a method for maintaining a population of foregut stem cells (FSCs), the method comprising:
  i) providing a population of foregut stem cells (FSCs);
  ii) culturing the population of FSCs in an FSC maintenance medium comprising a TGFβ ligand, preferably activin, fibroblast growth factor (FGF), bone morphogenetic protein (BMP), HGF, EGF, and Heparin.

Another aspect of the invention provides a method for differentiating a population of foregut stem cells (FSCs) into pulmonary progenitor cells, the method comprising:
  i) providing a population of foregut stem cells (FSCs);
  ii) culturing the population of FSCs in a first pulmonary induction medium comprising RA and FGF;
  iii) culturing the cells from step iii) in a second pulmonary induction medium comprising FGF and HGF;
  thereby producing a population of pulmonary progenitor cells.

Other aspects of the invention provide an isolated population of FSCs produced by a method described herein and the use of an isolated population of FSCs produced by a method described herein for in vitro differentiation into more differentiated endoderm cells.

BRIEF DESCRIPTION OF FIGURES

FIG. 1 shows that hPSCs derived foregut can self-renew in vitro.

FIG. 2 shows that hFSCs have the capacity to differentiate into multiple derivatives of the foregut. FIG. 2F shows immunostaining results which confirm that C-Peptide and PDX1 are expressed by cells differentiated for 25 days. FIG. 2G shows an example of a method to differentiate hFSCs into hepatic cells.

FIG. 3 shows that the generation of hFSCs overcomes variability between hIPSC lines.

DETAILED DESCRIPTION

Figure 1A:
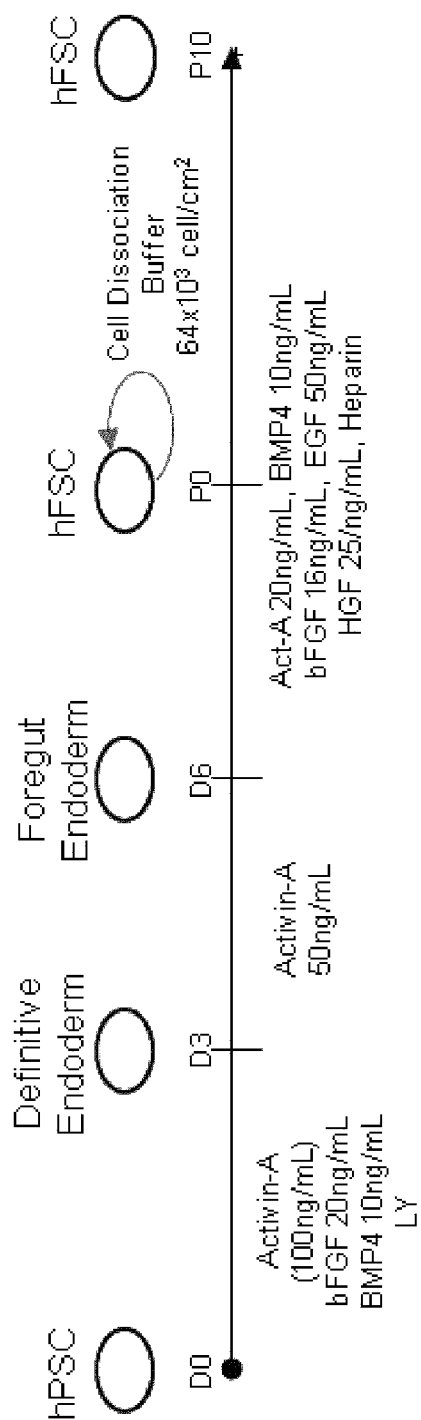
FIG. 1A shows the method to differentiate and to propagate Foregut Endoderm Stem Cells derived from hPSCs.

This invention relates to the in vitro production of foregut stem cells (FSCs) from populations of pluripotent cells. FSCs may be consistently produced from different pluripotent cell lines and are shown herein to be self-renewing and multipotent. FSCs may therefore be a useful source of multipotent cells for the in vitro production of cells of endodermal lineages, for example pulmonary, hepatic and pancreatic cells.

Foregut stem cells (FSCs) may be produced as described herein by culturing a population of definitive endoderm cells (DECs) in a foregut induction medium comprising a TGFβ ligand and allowing the DECs to differentiate into FSCs.

In some embodiments, foregut stem cells (FSCs) may be produced as described herein by culturing a population of pluripotent cells (PSCs) in a definitive endoderm induction medium to produce a population of cells comprising DECs and then culturing the population of cells in a foregut induction medium comprising a TGFβ ligand and allowing the DECs to differentiate into FSCs.

Pluripotent cells are cells which exhibit an undifferentiated phenotype and are potentially capable of differentiating into any foetal or adult cell type of any of the three germ layers (endoderm, mesoderm and endoderm). A pluripotent cell is distinct from a totipotent cell and cannot give rise to extraembryonic cell lineages. The population of pluripotent cells may be clonal i.e. genetically identical cells descended from a single common ancestor cell.

Pluripotent cells may express one or more of the following pluripotency associated markers: Oct4, Sox2, Alkaline Phosphatase, POU5f1, SSEA-3, Nanog, SSEA-4, Tra-1-60, KLF-4 and c-myc, preferably one or more of POU5f1, NANOG and SOX2. A pluripotent cell may lack markers associated with specific differentiative fates, such as Bra, Sox17, FoxA2, αFP, Sox1, NCAM, GATA6, GATA4, Hand1 and CDX2. In particular, a pluripotent cell may lack markers associated with endodermal fates.

Preferably, the pluripotent cells are human pluripotent cells.

Pluripotent cells may include embryonic stem cells (ESCs) and non-embryonic stem cells, for example foetal and adult stem cells, and induced pluripotent stem cells (IPSCs). In some embodiments, the pluripotent cells are not hESCs.

Embryonic stem cells may be obtained using conventional techniques. For example, ESCs cells may be obtained from a cultured ESC cell line, for example a hESC line. Numerous cultured hESC lines are publically available from repositories (e.g. NIH Human Embryonic Stem Cell Registry), such as CHB-1 to CHB-12, RUES1 to RUES3, HUES1 to HUES28, HUES45, HUES48, HUES49, HUES53, HUES62 to HUES66, WA01 (H1), WA07 (H7), WA09 (H9), WA13 (H13), WA14 (H14), NYUES1 to NYUES7, MFS5, and UCLA1 to UCLA3. Further examples of suitable human embryonic stem cell lines are described in Thomson J A et al Science 282: 1145-1147 (1998); Reubinoff et al. Nat Biotechnol 18:399-404 (2000); Cowan, C. A. et al. N. Engl. J. Med. 350, 1353-1356(2004), Gage, F. H., et al. Ann. Rev. Neurosci. 18 159-192 (1995); and Gotlieb (2002) Annu. Rev. Neurosci 25 381-407); Carpenter et al. Stem Cells. 5(1): 79-88 (2003). Potentially clinical grade hESCs are described in Klimanskaya, I. et al. Lancet 365, 1636-1641 (2005) and Ludwig, T. E. et al. Nat. Biotechnol. 24, 185-187 (2006). Suitable hESCs may be obtained for use in the invention without either destroying a human embryo or using a human embryo for an industrial or commercial purpose. For example, hESCs may be obtained by blastomere biopsy techniques (Klimanskaya (2013) Semin Reprod Med. 31(1):49-55; Klimanskaya et al Nature (2006) 444 (7118)481-5).

iPSCs are pluripotent cells which are derived from non-pluripotent, fully differentiated ancestor or antecedent cells. Suitable ancestor cells include somatic cells, such as adult fibroblasts and peripheral blood cells. Ancestor cells are typically reprogrammed by the introduction of pluripotency genes or proteins, such as Oct4, Sox2 and Sox1 into the cell. The genes or proteins may be introduced into the differentiated cells by any suitable technique, including plasmid or more preferably, viral transfection or direct protein delivery. Other genes, for example Kif genes, such as Kif-1, -2, -4 and -5; Myc genes such as C-myc, L-myc and N-myc; nanog; and Lin28 may also be introduced into the cell to increase induction efficiency. Following introduction of the pluripotency genes or proteins, the ancestor cells may be cultured. Cells expressing pluripotency markers may be isolated and/or purified to produce a population of iPSCs. Techniques for the production of iPSCs are well-known in the art (Yamanaka et al Nature 2007; 448:313-7; Yamanaka 6 2007 Jun. 7; 1(1):39-49; Kim et al Nature. 2008 Jul. 31; 454 (7204):646-50; Takahashi Cell. 2007 Nov. 30; 131(5):861-72. Park et al Nature. 2008 Jan. 10; 451(7175):141-6; Kim et et al Cell Stem Cell. 2009 Jun. 5; 4(6):472-6; Vallier, L., et al. Stem Cells, 2009. 9999(999A): p. N/A).

Figure 4:
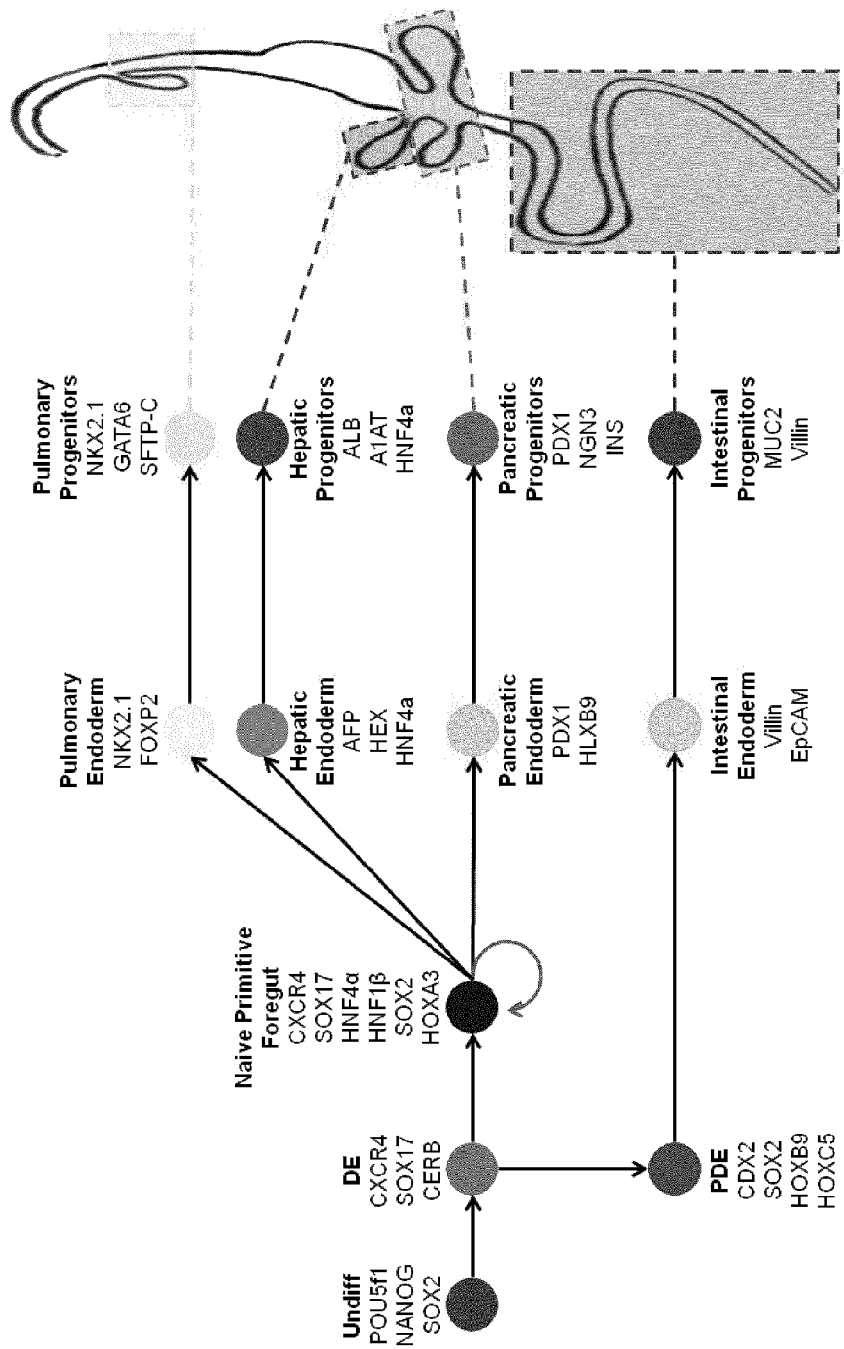
FIG. 4 shows a schematic of endoderm patterning and differentiation in vitro. The culture system described here represents a unique platform for generating a diversity of endodermal cells from the same original hPSC line. Indeed, DE generated from hPSCs can be patterned into hindgut endoderm that can further differentiate into intestinal epithelium or into self-renewable foregut endoderm cells which can be easily isolated by simple passaging. These Foregut Stem Cells can undergo prolonged passaging while retaining their capacity to differentiate into lung, liver and pancreatic cells.

Preferably, the pluripotent cells are IPSCs, more preferably human IPSCs (hIPSCs).

iPSCs may be derived from somatic cells, such as fibroblasts, which have a normal (i.e. non-disease associated) genotype, for example cells obtained from an individual without a genetic disorder. The iPSCs may be used as described herein to produce FSCs with a normal (i.e. non-disease associated) genotype. These FSCs may be further differentiated into pulmonary, pancreatic, hepatic or other endodermal lineages as shown in FIG. 4, which may be useful in therapy, modelling or other applications.

In some embodiments, the pluripotent cells may IPSCs which are refractory or resistant to endodermal differentiation, for example, due to epigenetic effects (Kim et al Nature (2010) 467 285-290). On differentiation in DE induction medium, endoderm resistant hIPSCs may produce a cell population with a low percentage of DECs (i.e. a heterogeneous cell population). Even cell populations with small number of DECs can be used to produce homogeneous FSC populations using the methods described herein.

The IPSCs may be obtained from an individual. In some embodiments, multiple populations of IPSCs may be obtained from a population of individuals and used to produce a panel of FSC populations as described herein.

In some embodiments, the iPSCs may be derived from somatic cells or other antecedent cells obtained from an individual with a distinct genetic background. For example, iPSCs may be produced from cells from an individual having a disease condition, an individual having a high risk of a disease condition and/or an individual with a low risk of a disease condition. Disease conditions may include disorders associated with endodermal tissue e.g. a pulmonary, hepatic or pancreatic condition. FSCs produced as described herein from individuals with distinct genetic backgrounds, or cells differentiated therefrom in vitro, may be useful in studying the mechanisms of disease conditions, such as diabetes and liver disease, and in identifying therapeutic targets.

iPSCs may be derived from somatic cells, such as fibroblasts, which have a disease-associated genotype, for example cells obtained from an individual with a genetic disorder. Genetic disorders may include disorders of endodermal tissue, such as pulmonary, pancreatic and hepatic disorders, and may be monogenetic disorders. Any cell with the disease genotype, for example a genetic mutation or defect, may be used to produce iPSCs, although samples of fibroblasts, e.g. dermal fibroblasts, may be conveniently obtained.

iPSCs which are produced from cells obtained from an individual with a genetic disorder may be used as described herein to produce FSCs which have the genotype of the genetic disorder. These FSCs may be further differentiated into pulmonary, pancreatic, hepatic or other endodermal lineages which possess the disease genotype. These endoderm cells may be useful, for example, in modelling the genetic disorder.

In some embodiments, a population of pluripotent cells may be obtained from a cultured pluripotent cell line. Conventional techniques may be employed for the culture and maintenance of human pluripotent cells (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)). Pluripotent cells for use in the present methods may be grown in defined conditions or on feeder cells. For example, pluripotent cells may be conventionally cultured in a culture dish on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Pluripotent cells for use in the present methods may be passaged by enzymatic or mechanical means.

Suitable culture media for pluripotent cells are well-known in the art and include; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml FGF2; or Knockout (KS) medium supplemented with 4 ng/ml FGF2; or KO-DMEM supplemented with 20% Serum Replacement, 1% Non-Essential Amino Acids, 1 mM L-Glutamine, 0.1 mM β-mercaptoethanol and 4 ng/ml to 10 ng/ml human FGF2; or DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin.

In preferred embodiments, a population of pluripotent cells for use in the present methods may be cultured in chemically defined medium (CDM).

A chemically defined medium (CDM) is a nutritive solution for culturing cells which contains only specified components, preferably components of known chemical structure. A CDM is devoid of undefined components or constituents which include undefined components, such as feeder cells, stromal cells, serum, matrigel, serum albumin and complex extracellular matrices. In some embodiments, the chemically defined medium is humanised. A humanised chemically defined medium is devoid of components or supplements derived or isolated from non-human animals, such as Foetal Bovine Serum (FBS) and Bovine Serum Albumin (BSA), and mouse feeder cells. Conditioned medium includes undefined components from cultured cells and is not chemically defined.

Suitable chemically defined basal medium, such as Advanced Dulbecco's modified eagle medium (DMEM) (Price et al Focus (2003) 25 3-6), Iscove's Modified Dulbecco's medium (IMDM) and RPMI-1640 (Moore, G. E. and Woods L. K., (1976) Tissue Culture Association Manual. 3, 503-508; see Table 1) are known in the art and available from commercial sources (e.g. Sigma-Aldrich MI USA; Life Technologies USA).

In some preferred embodiments, a population of pluripotent cells for use in the present methods may be cultured in a CDM which comprise a chemically defined basal medium supplemented with a serum-free media supplement and/or one or more additional components, for example transferrin, 1-thioglycerol and defined lipids and optionally polyvinyl alcohol; polyvinyl alcohol and insulin; serum albumin; or serum albumin and insulin.

Suitable serum-free media supplements include B27 (Brewer et al Brain Res (1989) 494 65-74; Brewer et al J. Neurosci Res 35 567-576 (1993); Brewer et al Focus 16 1 6-9; Brewer et al (1995) J. Neurosci. Res. 42:674-683; Roth et al J Trace Elem Med Biol (2010) 24 130-137) and NS21 (Chen et al J. Neurosci Meths (2008) 171 239-247). Serum-free media supplements, such as B27 and N21, are well known in the art and widely available commercially (e.g. Invitrogen; Sigma Aldrich Inc).

Suitable chemically defined media include CDM-PVA (Johansson and Wiles (1995) Mol Cell Biol 15, 141-151), which comprises a basal medium supplemented with polyvinyl alcohol, insulin, transferrin and defined lipids. For example, a CDM-PVA medium may consist of: 50% Iscove's Modified Dulbecco's Medium (IMDM) plus 50% Ham's F12 with GlutaMAX-1 ™ or 50% F12 NUT-MIX (Gibco, supplemented with 1% chemically defined lipid concentrate, 450 µM 1-thiolglycerol, 15 µg/ml transferrin, 1 mg/ml polyvinyl alcohol, 7 µg/ml Insulin. Other suitable chemically defined nutrient media include hESC maintenance medium (CDMA) which is identical to the CDM-PVA described above with the replacement of PVA with 5 mg/ml BSA; and RPMI basal medium supplemented with B27 and Activin (for example at least 50 ng/ml).

CDM-PVA media are described in Vallier et al 2009 PLoS ONE 4: e6082. doi: 10.1371; Vallier et al 2009 Stem Cells 27: 2655-2666, Touboul 2010 51: 1754-1765. Teo et al 2011 Genes & Dev. (2011) 25: 238-250 and Peterson & Loring Human Stem Cell Manual: A Laboratory Guide (2012) Academic Press.

In order to maintain pluripotency, the pluripotent cells may be maintained in CDM supplemented with Activin and FGF before differentiation. For example, a CDM may further comprise FGF2 (for example, 10 to 20 ng/ml, e.g. 12 ng/ml) and activin A (for example, 10 ng/ml) (Vallier et al. 2005 J Cell Sci 118:4495-4509; Brons et al Nature. (2007) July 12; 448(7150):191-5).

Suitable techniques for cell culture are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5% Carbon Dioxide. Media is preferably changed every two days and cells allowed to settle by gravity.

A population of pluripotent cells suitable for use in the present methods may be heterogeneous or may be substantially free from one or more other cell types (i.e. homogenous). Pluripotent cells may, for example, be separated from other cell types, using any technique known to those skilled in the art, including those based on the recognition of extracellular epitopes by antibodies and magnetic beads or fluorescence activated cell sorting (MACS or FACS) including the use of antibodies against extracellular regions of molecules found on stem cells, such as SSEA4.

The population of pluripotent cells is cultured in a definitive endoderm (DE) induction medium to produce a cell population that comprises DECs.

The DE induction medium is preferably a chemically defined medium (CDM).

A suitable DE induction medium may comprise a chemically defined nutrient medium and one or more differentiation factors.

The chemically defined nutrient medium may comprise or consist of a basal medium supplemented with one or more additional defined components, such as polyvinyl alcohol, 1-thioglycerol, insulin, transferrin and defined lipids.

Suitable chemically defined basal media are described above and include Iscove's Modified Dulbecco's Medium (IMDM), Ham's F12, Advanced Dulbecco's modified eagle medium (DMEM) (Price et al Focus (2003), 25 3-6), and RPMI-1640 (Moore, G. E. and Woods L. K., (1976) Tissue Culture Association Manual. 3, 503-508).

The basal medium may be supplemented by serum-free culture medium supplements and/or additional components in the DE induction medium. Suitable supplements and additional components are described above and may include L-glutamine or substitutes, such as GlutaMAX-1™, chemically defined lipids, albumin, 1-thiolglycerol, polyvinyl alcohol, insulin and transferrin.

Suitable chemically defined nutrient media for use in the DE induction medium include CDM-PVA and CDM-BA as described above.

Differentiation factors are factors which modulate, for example promote or inhibit, a signalling pathway which mediates differentiation in a mammalian cell. Differentiation factors may include growth factors, cytokines and inhibitors which modulate one or more of the Activin/Nodal, FGF, Wnt or BMP signalling pathways. Examples of differentiation factors include FGFs, BMPs, retinoic acid, TGFβ ligands, such as Activin, TGFβ or Nodal, GDFs, LIF, IL, activin and phosphatidylinositol 3-kinase (PI3K) inhibitors.

A differentiation factor may be present in a medium described herein in an amount that is effective to modulate a signalling pathway in cells cultured in the medium.

The DE induction medium may further comprise a TGFβ ligand, a fibroblast growth factor (FGF), a bone morphogenetic protein (BMP) and a PI3K inhibitor. The DE induction medium may be devoid of differentiation factors other than the TGFβ ligand, fibroblast growth factor (FGF), bone morphogenetic protein (BMP) and PI3K inhibitor [4, 6, 7, 9, 20]

The DE induction medium may consist of a chemically defined nutrient medium supplemented with an effective amount of a TGFβ ligand, fibroblast growth factor (FGF), bone morphogenetic protein (BMP) and a PI3K inhibitor. For example, the DE induction medium may consist of a chemically defined nutrient medium, such as CDM-PVA, supplemented with activin, fibroblast growth factor (FGF), bone morphogenetic protein (BMP) and LY294002.

A preferred DE induction medium may consist of CDM-PVA as described above supplemented with Activin-A (10 ng/mL to 1 ug/mL, preferably 100 ng/mL), BMP4 (1 to 100 ng/mL, preferably 10 ng/mL), bFGF (2 to 200 ng/ml preferably 20 ng/mL) and LY294002 (1 to 100 µM, preferably 10 µM).

In other embodiments, a DE induction medium may consist of RPMI supplemented with Activin and Wnt (KA D'Amour, Nat Biotech, 2005 December; 23(12):1534-41).

Alternatively, DECs may be produced from pluripotent cells by three dimensional cell culture in serum containing medium containing activin (Ogawa, S. Development 2013 August; 140(15):3285-96)).

TGFβ ligands are peptides of the TGFβ superfamily which stimulate SMAD2 and SMAD3 mediated intracellular signalling pathways in mammalian cells. Members of the TGFβ superfamily possess a characteristic structure and are well-known in the art.

The TGFβ ligand may be Activin, TGFβ, Nodal, GDF3, GDF8, GDF10 or GDF11, preferably activin.

Activin (Activin A: NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway (Vallier et al., *Cell Science* 118:4495-4509 (2005)). Activin is readily available from commercial sources (e.g. Stemgent Inc. MA USA). Conveniently, the concentration of Activin in a medium described herein may be from 10 to 1000 ng/ml, preferably about 100 ng/ml.

TGFβ (NCBI GeneID: 7040 nucleic acid reference sequence NM_000660.4 GI: 260655621, amino acid reference sequence NP_000651.3 GI: 63025222) is a homodimeric polypeptide which regulates proliferation and differentiation (Watabe, T. et al (2009). Cell Res. 19:103-115). Recombinant human TGFβ is readily available from commercial sources (e.g. Stemgent Inc. MA USA). Conveniently, the concentration of TGFβ in the medium may be from 10 to 1000 ng/ml, preferably about 100 ng/ml.

Nodal (NCBI GeneID 4838 nucleic acid sequence reference NM_018055.4 GI: 222352097, amino acid sequence reference NP_060525.3 GI: 222352098) is a member of the TGFβ superfamily which regulates differentiation (Hamada et al *Nat. Rev. Genet.* 3 (2): 103-13). Nodal is readily available from commercial sources (e.g. Abcam Ltd, UK). Conveniently, the concentration of Nodal in the medium may be from 10 to 1000 ng/ml, preferably about 100 ng/ml.

GDF3 (NCBI Gene ID 9573 nucleic acid sequence reference NM_020634.1 GI: 10190669, amino acid sequence reference NP_065685.1 GI: 10190670) is a member of TGFβ superfamily which is characterized by a polybasic proteolytic processing site that is cleaved to produce a mature GDF3 protein containing seven conserved cysteine residues. Conveniently, the concentration of GDF3 in the medium may be from 10 to 1000 ng/ml, preferably about 100 ng/ml.

GDF8 (also called MSTN; NCBI Gene ID 2660 nucleic acid sequence reference NM_005259.2 GI: 149408158, amino acid sequence reference NP_005250.1 GI: 4885259) is another member of TGFβ superfamily which is characterized by a polybasic proteolytic processing site that is cleaved to produce a mature GDF8 protein containing seven conserved cysteine residues. Conveniently, the concentration of GDF8 in the medium may be from 10 to 1000 ng/ml, preferably about 100 ng/ml (Hannan et al Cloning Stem Cells. 2009 September; 11(3):427-35).

GDF10 (also called BMP3B; NCBI Gene ID 2662 nucleic acid sequence reference NM_005811.3 GI: 223941867, amino acid sequence reference NP_004953.1 GI: 4826740) is another member of TGFβ superfamily which is characterized by a polybasic proteolytic processing site that is cleaved to produce a mature GDF8 protein containing seven conserved cysteine residues. Conveniently, the concentration of GDF8 in the medium may be from 10 to 1000 ng/ml, preferably about 100 ng/ml (Hannan et al Cloning Stem Cells. 2009 September; 11(3):427-35).

GDF11 (also called BMP11; NCBI Gene ID 10220 nucleic acid sequence reference NM_004962.3 GI: 325652088, amino acid sequence reference NP_005802.1 GI: 5031613) is another member of TGFβ superfamily which is characterized by a polybasic proteolytic processing site that is cleaved to produce a mature GDF8 protein containing seven conserved cysteine residues. Conveniently, the concentration of GDF8 in the medium may be from 10 to 1000 ng/ml, preferably about 100 ng/ml (Hannan et al Cloning Stem Cells. 2009 September; 11(3):427-35).

Fibroblast growth factor (FGF) is a protein factor which stimulates cellular growth, proliferation and cellular differentiation by binding to a fibroblast growth factor receptor (FGFR). Suitable fibroblast growth factors include any member of the FGF family, for example any one of FGF1 to FGF14 and FGF15 to FGF23.

Preferably, the FGF is FGF2 (also known as bFGF, NCBI GeneID: 2247, nucleic acid sequence NM_002006.3 GI: 41352694, amino acid sequence NP_001997.4 GI: 41352695); FGF7 (also known as keratinocyte growth factor (or KGF), NCBI GeneID: 2247, nucleic acid sequence NM_002006.3 GI: 41352694, amino acid sequence NP_001997.4 GI: 41352695); or FGF10 (NCBI GeneID: 2247, nucleic acid sequence NM_002006.3 GI: 41352694, amino acid sequence NP_001997.4 GI: 41352695). Most preferably, the fibroblast growth factor is FGF2.

Fibroblast growth factors, such as FGF2, FGF7 and FGF10, may be produced using routine recombinant techniques or obtained from commercial suppliers (e.g. R&D Systems, Minneapolis, Minn.; Stemgent Inc, USA).

Hepatocyte growth factor (HGF) (NCBI GeneID: 3082, nucleic acid sequence NM_000601.4 GI: 58533168, amino acid sequence NP_000592.3 GI: 33859835) is a cytokine which modulates cell growth, cell motility, and morphogenesis through binding to the c-Met receptor. Conveniently, the concentration of HGF in a cell culture medium may be from 5 to 500 ng/ml, preferably about 20 ng/ml or 50 ng/ml.

Hepatocyte growth factor (HGF) may be produced using routine recombinant techniques or obtained from commercial suppliers (e.g. R&D Systems, Minneapolis, Minn.; Stemgent Inc, USA).

Bone morphogenetic protein (BMP) Bone Morphogenic Proteins bind to Bone Morphogenic Protein Receptors (BMPRs) and stimulate intracellular signalling through pathways mediated by SMAD1, SMAD5 and SMAD9. Suitable Bone Morphogenic Proteins include any member of the BMP family, for example BMP2, BMP3, BMP4, BMP5, BMP6 or BMP7. Preferably the second TGFβ ligand is BMP2 (NCBI GeneID: 650, nucleic acid sequence NM_001200.2 GI: 80861484; amino acid sequence NP_001191.1 GI: 4557369) or BMP4 (NCBI GeneID: 652, nucleic acid sequence NM_001202.3 GI: 157276592; amino acid sequence NP_001193.2 GI: 157276593). Suitable BMPs include BMP4. Conveniently, the concentration of a Bone Morphogenic Protein, such as BMP2 or BMP4 in a medium described herein may be from 1 to 500 ng/ml, preferably about 10 ng/ml.

Bone Morphogenic Proteins may be produced using routine recombinant techniques or obtained from commercial suppliers (e.g. R&D, Minneapolis, USA, Stemgent Inc, USA).

Retinoic acid (2E,4E,6E,8E)-3,7-dimethyl-9-(2,6,6-trimethylcyclohexen-1-yl)nona-2,4,6,8-tetraenoic acid) is a metabolite of vitamin A that modulates transcription through binding to the retinoic acid receptor (RAR) and modulates differentiation in a range of cell types. Preferably all-trans retinoic acid is employed in media described herein.

Conveniently, the concentration of retinoic acid in a medium may be 1 to 10 μM of preferably about 2 μM.

Retinoic acid is available from commercial suppliers (e.g. Sigma Aldrich, USA; Stemgent Inc, USA).

PI3K inhibitors inhibit the activity of phosphatidylinositol 3-kinases, such as phosphatidylinositol-4,5-bisphosphate 3-kinase (EC2.7.1.153).

Suitable PI3K inhibitors include wortmannin; LY301497 (17-b-hydroxywortmannin); LY294002 (2-morpholin-4-yl-8-phenylchromen-4-one: Maclean et al (2007) Stem Cells 25

29-38); CLB1309 (KN309: (±)-2-({1-[7-methyl-2-(morpholin-4-yl)-4-oxo-pyrido[1,2-a]pyrimidin-9-yl]ethyl}amino) benzoic acid); PX-866 ((1E,4S,4aR,5R,6aS,9aR)-5-(Acetyloxy)-1-[(di-2-propen-1-ylamino)methylene]-4,4a,5,6,6a,8,9,9a-octahydro-11-hydroxy-4-(methoxymethyl)-4a,6a-dimethylcyclopenta [5,6]naphtho[1,2-c]pyran-2,7,10(1H)-trione); IC87114 (quinolone pyrrolopyrimidine); GDC-0941 (2-(1H-Indazol-4-yl)-6-[[4-(methylsulfonyl)-1-piperazinyl]methyl]-4-(4-morpholinyl)-thieno[3,2-d]pyrimidine); TGX-221 (7-methyl-2-(4-morpholinyl)-9-[1-(phenylamino) ethyl]-4H-pyrido[1,2-a]pyrimidin-4-one), quercetin; BEZ235; XL147; X1765; PX-866; ZSTK474 (2-(2-difluoromethylbenzimidazol-1-yl)4,6-dimorpholino-1,3,5-triazine); and SF1126 (2-[2-methoxyethylamino]-8-phenyl-4H-1-benzopyran-4-one). Other PI3K inhibitors are available in the art.

In some preferred embodiments, the PI3K inhibitor is LY294002.

Suitable PI3K inhibitors may be obtained from commercial suppliers (e.g. Calbiochem CA USA).

For example, a medium may contain 1 to 100 μM PI3K inhibitor, such as LY294002, preferably about 10 μM.

The human pluripotent cells may be cultured in the DE induction medium for 1 to 6 days, preferably about 3 days, to produce a population of cells comprising definitive endoderm cells (DECs).

The pluripotent cells differentiate in the DE induction medium into a cell population that comprises or consists of definitive endoderm cells (DECs).

In some embodiments, the cell population may be a homogeneous or substantially homogeneous population of DECs. For example, 80% or more, 90% or more, 95% or more, 98% or more or most preferably all of the cells in the cell population may be DECs.

In other embodiments, the cell population may be a heterogeneous population which comprises DECs and one or more other cell types. For example, 40% or less, 30% or less, 20% or less, or 10% or less of the cells in the cell population may be DECs.

In addition to DECs, the population may comprise fibroblasts, mesodermal, ectodermal, trophectodermal and/or pluripotent cells.

DECs are early stage cells of the endodermal lineage. DECs have reduced differentiation potential compared to a pluripotent cell and exhibit a partially differentiated endodermal phenotype. DECs are committed to lineages in the endoderm primary germ layer and are potentially capable of further differentiation into any foetal or adult cell type of the endodermal germ layer. For example, a DEC may differentiate under appropriate conditions into all cell types in the liver, pancreas, lungs, gut, and thyroid. In some embodiments, DECs may be termed "multipotent". DECs cannot give rise to extraembryonic, mesoderm or neuroectoderm cell lineages.

DECs may express Sox17, foxA2, GSC, Mixl1, Lhx1, CXCR4, GATA4, eomesodermin (EOMES), Mixl1, HNF-3 beta, Cerberus, OTX4, goosecoid, C-kit, CD99, and Hex. Typically, DECs are characterised by the expression of CXCR4 and Sox17.

DECs may lack markers associated with specific endodermal lineages for example gut, pancreas, liver or lung markers. For example, DECs may not express SOX2 (foregut), CDX2 (mid-hind gut), PDX1, PTF1a (pancreas), AFP (liver), Nkx2.1 or TBX1 (lung).

DECs may also lack markers associated with pluripotency, such as Oct4, Sox2, Alkaline Phosphatase, POU5f1, SSEA-3, Nanog, SSEA-4, Tra-1-60, KLF-4 and c-myc, as well as markers associated with extraembryonic, mesoderm or neuroectoderm cell lineages.

The cell population comprising DECs is cultured in the foregut induction medium such that the DECs differentiate into FSCs.

The foregut induction medium is preferably a chemically defined medium (CDM).

A suitable foregut induction medium may comprise a chemically defined nutrient medium and one or more differentiation factors. Suitable chemically defined nutrient media are described in more detail above. For example, a foregut induction medium may comprise a basal medium, such as RPMI, supplemented with a serum free medium supplement, such as B27.

The foregut induction medium may further comprise a TGFβ ligand, preferably activin. For example, the medium may comprise Activin-A.

The TGFβ ligand may be present in the medium in an effective amount, for example at 5 to 500 ng/mL, preferably 50 ng/mL.

The foregut induction medium may be devoid of differentiation factors other than the TGFβ ligand. For example, the foregut induction medium may consist of a chemically defined nutrient medium supplemented with the TGFβ ligand. Preferably, the TGFβ ligand is activin.

Preferably the foregut induction medium contains suitable differentiation factors to stimulate TGFβ signalling pathways in the cells, but not to stimulate other signalling pathways, such as Wnt signalling.

In some embodiments, the foregut induction medium may be devoid of BMP antagonists, such as noggin, and activin/TGFβ antagonists, such as SB431542.

The cell population comprising DECs may be cultured in the foregut induction medium for 2 to 5 days, preferably 3-4 days to allow the DECs to differentiate into FSCs.

FSCs may express one or more, preferably all of HNF4α, SOX17, CXCR4, EpCAM, HNF1β, GATA4, Cer, HNF6, HNF1beta, SOX2, HHEX, and HOXA3. For example, at least 50% of the cells in the population may express SOX2, HHEX, and HOXA3.

FSCs may lack expression of CDX2 or HOXC5. FSCs may also lack expression of pluripotency markers, such as Oct4, Sox2, alkaline phosphatase, SSEA-3, Nanog, SSEA-4, Tra-1-60, KLF-4 and POU5f1, and markers associated with ectodermal or mesodermal lineages.

FSCs may lack expression of endodermal tissue markers, for example pulmonary markers, such as NKX2.1, hepatic markers, such as AFP, or pancreatic markers, such as PDX1 markers.

The extent of differentiation of the cell population comprising DECs may be determined during cell culture by monitoring and/or detecting the expression of one or more cell markers in the population of differentiating cells. For example, an increase in the expression of markers characteristic of FSCs or a decrease in the expression of markers characteristic of DECs may be determined.

The expression of cell markers may be determined by any suitable technique, including immunocytochemistry, immunofluorescence, RT-PCR, immunoblotting, fluorescence-activated cell sorting (FACS), and enzymatic analysis.

The methods described above may further comprise monitoring and/or detecting the presence of one or more FSC markers and/or the absence of one or more DEC in the population of cells.

The methods described above may further comprise identifying one or more cells in the population as FSC, for example from the presence of expression of one or more FSC markers.

In some embodiments, for example when the cell population is a substantially homogeneous population of DECs, differentiation of the DECs in the cell population as described herein may produce a population of FSCs which is substantially free from other cell types. For example, the population may contain 85% or more, 90% or more, 95% or more, or 98% or more FSCs, following culture in the foregut induction medium.

Preferably, the population of FSCs is sufficiently free of other cell types that no purification is required.

In other embodiments, for example when the cell population is a heterogeneous population that comprises other cell types, such as fibroblasts, ectodermal cells, mesodermal cells, pluripotent cells, and trophectoderm cells, as well as FSCs, the population may contain 60% or less, 50% or less, 40% or less, or 30% or less FSCs, following culture in the foregut induction medium.

If required, the FSCs may be separated from other cell types in the population using any technique known to those skilled in the art, including those based on the recognition of extracellular epitopes by antibodies and magnetic beads or fluorescence activated cell sorting (MACS or FACS) including the use of antibodies against extracellular regions of characteristic markers as described above.

In preferred embodiments, FSCs may be separated from other cell types in the population by culturing in an FSC maintenance medium, as described herein. For example, a substantially homogeneous or pure population of FSCs may be produced by five or more passages in the FSC maintenance medium.

Another aspect of the invention provides a population of isolated FSCs, preferably a population of isolated FSCs produced by a method described above.

As described above, each FSC in the isolated population is able to self-renew in vitro. Each FSC is also multipotent and capable of differentiation into any one of pulmonary, hepatic and pancreatic cell lineages (i.e. is not lineage restricted). FSCs produced by the methods described herein do not have anterior or posterior foregut identity and may differentiate into both anterior and posterior foregut lineages. FSCs thus possess greater differentiation capacity than anterior or posterior foregut progenitor cells.

FSCs as described herein are culturable and can be serially expanded in vitro whilst retaining their ability to differentiate (i.e. FSCs remain multipotent). The isolation of a stable population of FSCs that can be maintained in vitro has not been reported previously.

Preferably, the population of hFSCs is homogeneous or substantially homogenous.

The isolated FSCs may have be produced by an iPSC derived from an individual and may have the same genotype as the individual. For example, the FSCs may have a disease associated genotype, for example an endodermal condition associated genotype.

As well as being self-renewing and multipotent, populations of FSCs produced as described herein are homogeneous and non-tumorigenic as demonstrated by teratoma assays and may be useful in the production of endodermal cells. In particular, FSCs may be useful in the production of large numbers of clinically relevant cells for regenerative medicine or other applications.

Another aspect of the invention provides the use of a population of isolated FSCs produced as described above for the in vitro production of endodermal cells.

Following culture in the foregut induction medium, a population of FSCs may be isolated, cultured, expanded or maintained.

In some preferred embodiments, the population of FSCs may be cultured in an FSC maintenance medium. This may be particularly useful in enriching the population for FSCs and depleting the population of non-FSCs.

The FSC maintenance medium is a chemically defined medium.

A suitable FSC maintenance medium may comprise a chemically defined nutrient medium and one or more differentiation factors.

Suitable chemically defined nutrient media are described above. For example, a suitable chemically defined nutrient medium for use in a FSC maintenance medium may comprise or consist of a basal medium, such as RPMI, supplemented with B27.

The FSC maintenance medium may further comprise a TGFβ ligand, preferably activin, fibroblast growth factor (FGF), bone morphogenetic protein (BMP), HGF, EGF, and Heparin.

Another aspect of the invention provides a method for maintaining a population of foregut stem cells (FSCs), the method comprising:
  i) providing a population of foregut stem cells (FSCs); and,
  ii) culturing the population of FSCs in an FSC maintenance medium comprising a TGFβ ligand, preferably activin, fibroblast growth factor (FGF), bone morphogenetic protein (BMP), HGF, EGF, and Heparin.

In some embodiments, the FSC maintenance medium may be devoid of differentiation factors other than a TGFβ ligand, fibroblast growth factor (FGF), bone morphogenetic protein (BMP), HGF, EGF, and heparin. For example, the FSC maintenance medium may consist of a chemically defined nutrient medium supplemented with a TGFβ ligand, fibroblast growth factor (FGF), bone morphogenetic protein (BMP), HGF, EGF, and Heparin. Preferably, the TGFβ ligand is activin.

The FSC maintenance medium may comprise or consist of a RPMI basal medium supplemented with B27 and the differentiation factors Activin-A (for example at 1 to 100 ng/mL, preferably 10 ng/mL), bFGF (for example at 2 to 200 ng/mL, preferably 20 ng/mL), BMP (for example at 1 to 100 ng/mL, preferably 10 ng/mL), HGF (for example at 2 to 200 ng/mL, preferably 20 ng/mL), EGF (for example at 5 to 500 ng/mL, preferably 50 ng/mL), and heparin (0.1 ug to 10 ug, preferably 1 ug).

Preferably, the population of FSCs is passaged at least five times in the FSC maintenance medium.

Passage of the population of FSCs in the FSC maintenance medium enriches the FSC content of the population and depletes the non-FSC content of the population. For example, after five passages in the maintenance medium, the population may contain at least 90%, at least 95%, at least 98% or preferably 100% FSCs.

Following production and optionally maintenance as described above, a population of FSCs may be stored or kept for subsequent use.

A population of FSCs may be further differentiated into more specific endodermal lineages and/or differentiated endoderm cells. For example, the FSCs may be differentiated into cells of a pancreatic lineage, such as pancreatic endoderm cells (PDX$^+$, HLXB9$^+$), or pancreatic progenitors (PDX$^+$, NGN3$^+$, INS$^+$), cells of a hepatic lineage, such as hepatic endoderm cells (AFP$^+$, HEX$^+$, HNF4a$^+$) or hepatic progenitors (Alb$^+$, A1AT$^+$, HNF4a$^+$) or cells of a pulmonary lineage, such as pulmonary endoderm cells (NKX2.1$^+$, FOXP2$^+$) and pulmonary progenitors (NKX2.1$^+$, GATA6$^+$, SFTP-C$^+$).

The use of FSCs as a differentiation substrate allows endodermal cells to be consistently produced from pluripotent cell populations irrespective of source. In particular, endoderm cells may consistently produced from iPSC lines that are refractory to endoderm differentiation.

The population of endodermal cells produced by differentiation of PSCs may be isolated, cultured, expanded or maintained.

In some embodiments, the population of definitive endoderm cells may be differentiated into cells of a hepatic lineage, for example hepatocytes, hepatic progenitor cells or hepatic endoderm cells. Suitable methods for hepatic differentiation are available in the art (see for example WO2012/025725; Yusa et al Nature. 2011 Oct. 12; 478 (7369):391-4; Cho et al Diabetologia. 2012 December; 55(12):3284-95; Hannan et al Nat Protoc. 2013 Jan. 31; 8(2):430-7; Touboul et al Hepatology. 2010 May; 51(5): 1754-65; Si-Tayeb et al Hepatology. 2010 January; 51(1): 297-305; Song et al Cell Res. 2009 November; 19(11):1233-42; Zhao et al PLoS One. 2009 Jul. 31; 4(7):e6468; Hay et al Proc Natl Acad Sci USA. 2008 Aug. 26; 105(34):12301-6. Baharvand et al Differentiation. 2008 May; 76(5):465-77. Agarwal et al Stem Cells. 2008 May; 26(5):1117-27. Cai et al Hepatology. 2007 May; 45(5):1229-39; Cai, J., et al *J Mol Cell Biol* 2(1): 50-60; D'Amour, K. A. et al (2006), *Nat Biotechnol* 24(11): 1392-401; Jiang, W. et al. (2007) *Cell Res* 17(4): 333-44.

In brief, any one of methods described above may further comprise;
culturing the population of FSCs produced as described above in a hepatic induction medium to produce a population of hepatic progenitor cells,
wherein the hepatic induction medium is a chemically defined medium which comprises BMP and FGF.

A suitable hepatic induction medium may comprise a chemically defined basal medium supplemented with one or more additional factors, preferably recombinant human factors, which induce the FSCs to differentiate into hepatic progenitor cells.

Suitable chemically defined basal media include RPMI-1640, which is described above, preferably supplemented with B27 supplement. The CDM may be supplemented with BMP, preferably BMP4, (e.g. 1 to 100 ng/mL, preferably 10 ng/mL) and FGF, preferably FGF10 (e.g. 1 to 100 ng/mL, preferably 10 ng/mL).

The population of FSCs may be cultured for 3 to 5 days, preferably about 4 days, to produce the population of hepatic progenitor cells.

Optionally, the hepatic progenitor cells may be further differentiated. For example, a method may further comprise culturing the population of hepatic progenitor cells in a hepatic maturation medium to produce a population of hepatocytes.

A suitable hepatic maturation medium may consist of a chemically defined basal medium supplemented with a serum free media supplement, such as B27, and optionally with additional factors, preferably recombinant human factors, to induce the hepatic progenitor cells to mature into hepatic progenitor cells. Suitable chemically defined basal media include CMRL, hepatozyme SFM. (GIBCO™; Invitrogen Inc) and Hepatocyte basal medium (Lonza). CMRL basal medium is a serum-free basal medium which is well known in the art and readily available from commercial sources (e.g. Cat No: 11530037 Invitrogen; Product #C0422 Sigma). Hepatozyme SFM is a serum-free basal medium which is available from commercial sources (e.g. Cat No 17705; Invitrogen).

The chemically defined basal medium may be supplemented with one or more factors which induce differentiation and maturation of hepatic progenitors into hepatocytes. For example, the basal medium may be supplemented with hepatocyte growth factor (HGF) or epidermal growth factor (EGF), for example at 5 to 500 ng/mL, preferably 50 ng/mL). The chemically defined basal medium may also be supplemented with one or more factors which induce differentiation and maturation of hepatocyte, such as oncostatin-M.

A suitable maturation medium may comprise a chemically defined basal medium, such as Hepatocyte Basal Medium or Hepatozyme SFM supplemented with a serum free media supplement, such as B27, and further supplemented with Oncostatin M (e.g. at 50 ng/mL) and HGF (e.g. at 50 ng/mL).

The population of hepatic progenitor cells may be cultured for 10 to 40 days, preferably about 25 days, to produce the population of hepatocytes.

Suitable techniques, media and reagents for differentiation into hepatic progenitors and hepatocytes are described in WO2012/025725; Yusa et al Nature. 2011 Oct 12; 478 (7369):391-4 and Cho et al Diabetologia. 2012 December; 55(12):3284-95.

In some embodiments, the population of FSCs may be differentiated into pancreatic endoderm or progenitor cells. Suitable methods for pancreatic differentiation are available in the art (see for example Cho et al Diabetologia. 2012 December; 55(12):3284-95; D'Amour et al., 2006), Jiang et al., 2007, Cai et al., 2010).

In brief, methods described above may further comprise;
culturing the population of FSCs in a first pancreatic induction medium comprising an activin antagonist; FGF; retinoic acid; and a BMP inhibitor to produce a population of dorsal foregut cells;
culturing the dorsal foregut cells in a second pancreatic induction medium comprising FGF, retinoic acid, a BMP inhibitor, and a hedgehog signalling inhibitor and then;
culturing the cells in a third pancreatic induction medium differentiation factors comprising FGF;
thereby producing a population of pancreatic progenitor cells.

A suitable first pancreatic induction medium may be a chemically defined medium (CDM) which comprises an activin/TGFβ antagonist; FGF; retinoic acid; and a BMP antagonist. In some embodiments, these may be the only differentiation factors in the medium. For example, the first pancreatic induction medium may consist of a chemically defined basal medium, such as advanced DMEM, supplemented with an activin/TGFβ antagonist, preferably SB-431542 (for example, 5 to 25 µM, preferably about 10 µM), FGF, preferably FGF10 (for example 5 to 100 ng/ml, preferably about 50 ng/ml), retinoic acid (for example at 0.5 to 20 µM, preferably about 2 µM) and a BMP antagonist, preferably noggin (for example 100 to 500 ng/ml).

Preferably, the population of FSCs may be cultured for 2 to 4 days, most preferably 3 days to produce the population of dorsal foregut cells.

A suitable second pancreatic induction medium may be a chemically defined medium (CDM) which comprises FGF, a BMP inhibitor, retinoic acid, and a hedgehog signalling inhibitor. In some embodiments, these may be the only differentiation factors in the medium. For example, the second pancreatic induction medium may consist of a chemically defined basal medium, such as advanced DMEM, supplemented with an FGF, preferably FGF10 (for example at 5 to 100 ng/ml, preferably about 50 ng/ml); retinoic acid, (for example at 0.5 to 20 µM, preferably about 2 µM); hedgehog signalling inhibitor, preferably KAAD-cyclopamine (for example 0.1 to 1 µM, preferably 0.25 µM); and a BMP antagonist, preferably noggin (for example 5 to 500 ng/ml or 100 to 500 ng/ml, preferably about 50 ng/ml).

The dorsal foregut cells may be cultured in the second pancreatic induction medium for 2 to 4 days, most preferably 3 days.

A suitable third pancreatic induction medium may be a chemically defined medium (CDM) which comprises FGF. In some embodiments, FGF may be the only differentiation factor in the medium. For example, the third pancreatic induction medium may consist of a chemically defined basal medium, such as advanced DMEM, supplemented with an FGF, preferably FGF10 (for example at 5 to 100 ng/ml, preferably about 50 ng/ml).

The cells may be cultured in the third pancreatic induction medium for 2 to 4 days, most preferably 3 days to produce a population of pancreatic progenitor cells.

Optionally, the pancreatic progenitor cells may be further differentiated and/or matured into pancreatic endocrine cells. For example, pancreatic cells may be matured by i) culturing in a first endocrine induction medium and ii) culturing in a second endocrine induction medium to produce the population of pancreatic endocrine cells,
  wherein the first endocrine induction medium is a chemically defined medium comprising a Notch signalling inhibitor and retinoic acid; and the second endocrine induction medium is a chemically defined medium devoid of differentiation factors other than retinoic acid.

A suitable first endocrine induction medium may be a chemically defined medium (CDM) supplemented with a serum-free media supplement, such as B27; which further comprises a Notch signalling inhibitor and retinoic acid. In some embodiments, the Notch signalling inhibitor and retinoic acid may be the only differentiation factors in the medium. The first endocrine induction medium may consist of a chemically defined basal medium, such as advanced DMEM, supplemented with B27 and Notch signalling inhibitor, preferably N-[N-(3,5-difluorophenacetyl)-1-alanyl]-S-phenylglycine t-butyl ester (DAPT) (for example at 0.1 to 10 mM, preferably about 1 mM).

The pancreatic progenitor cells may be cultured in the first endocrine induction medium for 2 to 4 days, most preferably 3 days.

A suitable second endocrine induction medium may be a chemically defined medium (CDM), such as advanced DMEM, supplemented with B27, without additional differentiation factors.

The pancreatic progenitor cells may be cultured in the second endocrine induction medium for 2 to 4 days, most preferably 3 days.

The pancreatic cells produced by the method may express pancreatic markers, such as PDX1, INS, NGN2, NGN3 and SST.

At least 80% of the cells may express PDX1 in the first endocrine induction medium. The cells may sequentially express early pancreatic markers (HLXB9, PDX1), then endocrine progenitor marker (Ngn3) and finally beta cell marker (Insulin).

Suitable protocols, reagents and media for the differentiation and maturation of pancreatic endocrine cells are available the art (see Kroon E et al. (2008) Nat Biotechnol 26: 443-452 and Cho et al Diabetologia. 2012 December; 55(12):3284-95).

In some embodiments, the population of FSCs may be differentiated into cells of pulmonary lineage, for example pulmonary progenitor cells or pulmonary endoderm cells.

FSCs may be differentiated into pulmonary cells by culturing in conditions inductive for pulmonary specification. For example, the FSCs may be differentiated into pulmonary cells by a method comprising;
  iii) culturing the population of FSCs in a first pulmonary induction medium comprising RA and FGF;
  iv) culturing the cells from step iii) in a second pulmonary induction medium comprising FGF and HGF;
  thereby producing a population of pulmonary progenitor cells.

A suitable first pulmonary induction medium may be a chemically defined medium (CDM) which comprises FGF and RA. In some embodiments, FGF and RA may be the only differentiation factors in the medium. For example, the first pulmonary induction medium may consist of a chemically defined basal medium, such as advanced DMEM, supplemented with an FGF, preferably FGF10 (for example at 10 to 1000 ng/ml, preferably about 100 ng/ml) and retinoic acid (for example at 0.3 to 30 uM, preferably about 3 uM).

The pulmonary progenitor cells may express early pulmonary markers Nkx2.1, FOXP2 and IRX1.

The pulmonary progenitor cells may express lung type II alveoli cell markers NKX2.1, ABCA3, MUC1 and distal airway markers NKX2.1, CK18, CFTR, SFTPC, GATA6.

In some preferred embodiments, the pulmonary progenitor cells may be type II pneumocytes expressing surfactant protein-C, mucin 1 and NKX2.1. The pulmonary progenitor cells may display one or more activities of a type II pneumocyte, for example ion-transfer via the cystic fibrosis transmembrane receptor and ability to differentiate into type I pneumocytes.

Other aspects of the invention provides an isolated population of type II pneumocytes and the use of FSCs in a method of producing a population of type II pneumocytes, for example a method described above.

A population of isolated FSCs produced as described herein may be useful in screening.

Another aspect of the invention provides a method of screening a compound comprising;
  contacting isolated FSCs as described above with a test compound, and;
  determining the effect of the test compound on said foregut stem cells and/or the effect of said foregut stem cells on the test compound.

The proliferation, growth or viability of FSCs or their ability to differentiate or perform one or more cell functions may be determined in the presence relative to the absence of the test compound. A decrease in differentiation, proliferation, growth, viability or ability to perform one or more cell functions is indicative that the compound has a toxic effect and an increase in growth, viability or ability to perform one or more cell functions is indicative that the compound has an ameliorative effect Cell populations produced from isolated FSCs may also be useful in screening. For example, a method of screening a compound may comprise;

contacting isolated hepatic, pancreatic or pulmonary progenitor cells produced as described above with a test compound, and;

determining the effect of the test compound on said progenitor cells and/or the effect of said progenitor cells on the test compound.

Another aspect of the invention provides a kit for production of FSCs comprising;

a foregut induction medium as described above, for example a CDM medium consisting of a chemically defined nutrient medium supplemented with a TGFβ ligand, preferably activin.

The kit may further comprise a DE induction medium as described above, for example a medium consisting of a chemically defined nutrient medium supplemented with a TGFβ ligand, fibroblast growth factor (FGF), bone morphogenetic protein (BMP) and a PI3K inhibitor.

The kit may further comprise a FSC maintenance medium as described above, for example a medium that consists of a chemically defined nutrient medium supplemented with a TGFβ ligand, preferably activin, fibroblast growth factor (FGF), bone morphogenetic protein (BMP), HGF, EGF, and Heparin.

The kit may further comprise one or more of; a hepatic induction medium, a hepatic maturation medium, a first pancreatic induction medium, a second pancreatic induction medium, a third pancreatic induction medium, a first endocrine induction medium, a second endocrine indiction medium, a first pulmonary induction medium and a second pulmonary induction medium. Suitable media are described described above.

Another aspect of the invention provides a kit for maintenance of FSCs comprising;

an FSC maintenance medium that consists of a chemically defined nutrient medium supplemented with an effective amount of a TGFβ ligand, preferably activin, fibroblast growth factor (FGF), bone morphogenetic protein (BMP), HGF, EGF, and Heparin.

Media may be supplemented with effective amounts of the differentiation factors set out above, as described elsewhere herein.

The one or more culture media in the kit may be formulated in deionized, distilled water. The one or more media will typically be sterilized prior to use to prevent contamination, e.g. by ultraviolet light, heating, irradiation or filtration. The one or more media may be frozen (e.g. at −20° C. or −80° C.) for storage or transport. The one or more media may contain one or more antibiotics to prevent contamination.

The one or more media may be a 1× formulation or a more concentrated formulation, e.g. a 2× to 250× concentrated medium formulation. In a 1× formulation each ingredient in the medium is at the concentration intended for cell culture, for example a concentration set out above. In a concentrated formulation one or more of the ingredients is present at a higher concentration than intended for cell culture. Concentrated culture media are well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

The one or more media in the kit may be contained in hermetically-sealed vessels. Hermetically-sealed vessels may be preferred for transport or storage of the culture media, to prevent contamination. The vessel may be any suitable vessel, such as a flask, a plate, a bottle, a jar, a vial or a bag.

Another aspect of the invention provides the use of a foregut induction medium as described herein in the in vitro differentiation of DECs into FSCs.

Another aspect of the invention provides the use of a foregut induction medium and a DE induction medium as described herein in the in vitro differentiation of pluripotent cells into FSCs.

Another aspect of the invention provides the use of an FSC maintenance medium as described herein for the in vitro culture of FSCs.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

EXPERIMENTS

Methods
Human ES and IPS Cell Culture hESCs (H9) and hIPSCs (BBHX8, A1ATD-1, COXV3, COXS8, Line4 and IPS40) were cultured in a chemically defined, feeder-free culture system as described previously using Activin-A (10 ng/mL) and bFGF (12 ng/mL)[5-7, 17, 18]. Cells were passaged every seven days using a mixture of collagenase IV or collagenase and dispase at a ratio of 1:1.

Differentiation of hPSCs into Endoderm

Cells were differentiated into definitive endoderm using CDM-PVA and Activin-A (100 ng/mL), BMP4 (10 ng/mL), bFGF (20 ng/mL), LY294002 (10 μM) for 3 days as described previously [4, 6, 7, 9].

Patterning of Definitive Endoderm

DE cells were cultured in RPMI+B27 medium with Activin-A (50 ng/mL) for 3-4 days to generate foregut cells. DE cells were cultured in RPMI+B27 medium with CHIR99021 (6 μM) for 4 days to generate posterior endoderm.

Differentiation of Posterior Endoderm into 3D Gut Organoids

Posteriorised endodermal cells were embedded in growth factor-reduced Matrigel (BD Biosciences) containing, B27 supplement (RA-depleted) (Invitrogen), human R-spondin (500 ng/mL) (R&D), human Noggin (100 ng/mL) (R&D), human EGF (100 ng/mL) (R&D), Jagged-1 peptide (1 µM) (AnaSpec Inc.). Cell/Matrigel mix was overlayed with Advanced DMEM/F12 (Gibco) supplemented with 2 mM GlutaMax (Invitrogen), 10 mM Hepes (Invitrogen) and 100 U/ml Penicillin/100 ug/ml Streptomycin) containing B27 supplement (RA-depleted) (Invitrogen), Y-27632, (10 uM) (Sigma Aldrich), Noggin (100 ng/ml) (R&D), human EGF (100 ng/ml) (R&D), human R-spondin (1 ug/ml) (R&D), human Wnt3a (100 ng/mL) (R&D)

Passaging and Maintenance of hFSCs hFSCs were cultured on gelatine coated plates prepared as described for hPSC maintenance in RPMI medium containing B27 Supplement, NEAA, Pen/Strep, Activin-A (10 ng/mL), bFGF (20 ng/mL), BMP (10 ng/mL), HGF (20 ng/mL), EGF (50 ng/mL), and Heparin. Cells were passaged every 4-7 days using cell dissociation buffer (CDB). Cells were washed 1× with PBS then incubated in CDB at 37° C. for 10-15 minutes. Cells were scraped as small clumps and transferred to a 15 mL tube and centrifuged at 800 rpm for 2 minutes. Cells were washed 1× with RPMI medium and then resuspended in RPMI medium containing the cocktails of growth factors described above and the Rock Inhibitor Y-27632 (10 µM). Rock inhibitor was not used during subsequent days of culture. Medium was changed the following day and every subsequent day until cells were 80-90% confluent.

Differentiation of hFSCs into Hepatic Endoderm

Hepatic differentiation has been described previously [4, 7, 9]. Briefly, hFSC's were cultured in RPMI+B27 containing BMP4 (10 ng/mL) and FGF10 (10 ng/mL) for four days. Cells were then cultured in Hepatocyte Basal Medium (Lonza) containing OSM (50 ng/mL) and HGF (50 ng/mL) for at least an additional 20 days.

Differentiation of hFSCs into Pancreatic Endoderm hFSCs were differentiated into pancreatic endoderm using a 5 step process as described previously[4]. hFSCs (stage 1) were cultured in Advanced DMEM (Invitrogen) supplemented with SB-431542 (10 µM; Tocris), FGF10 (50 ng/ml; AutogenBioclear), all-trans retinoic acid (RA, 2 µM; Sigma) and Noggin (50 ng/ml; R&D Systems) for 3 days. For stage 2, the cells were cultured in Advanced DMEM supplemented with human FGF10 (50 ng/ml; AutogenBioclear), all-trans retinoic acid (RA, 2 uM; Sigma), KAAD-cyclopamine (0.25 uM; Toronto Research Chemicals) and Noggin (50 ng/ml; R&D Systems) for 3 days. For Stage 3, the cells were cultured in human FGF10 (50 ng/ml; R&D Systems) for 3 days. For maturation of pancreatic progenitors (Stage 4), cells were grown in Advanced DMEM+1% vol/vol B27 and DAPT (1 mM) for 3 days and for 3 additional days in Advanced DMEM+1% vol/vol B27 (Stage 5). Stage 4 and the final stage, Stage 5 of differentiation, was achieved using medium devoid of insulin so as not to interfere with immunofluorescent and ELISA assays. Antibodies to demonstrate presence of insulin were raised against C-peptide to avoid potential false-positive results.

Differentiation of hFSCs into Lung Endoderm

Lung progenitor cells were generated by growing hFSCs in retinoic acid (3 µM) and FGF10 (100 ng/mL) for 6 days. Cells were either grown in 2D culture with FGF10, and HGF or in 3D Matrigel culture using, FGF10 and HGF for an addition 20 days RNA Isolation, RT and Q-PCR RNA was isolated using the GenElute (Sigma-Aldrich) mammalian total RNA isolation kit. Adherent or cell pellets were washed 1× with PBS and then lysed in 350 uL of total-RNA lysis buffer. RNA was then purified as per the manufacturer's instructions. DNA digestion was performed using RNAase-free DNase (Sigma) as per the manufacturer's recommendations. 500 ng of total RNA was reverse transcribed using 500 ng total RNA, 0.5 uL random primers (Promega) and 1 uL of dNTP's (Promega) per reaction. Samples were heated to 65° C. for 5 minutes and then placed on ice for a further 5 minutes. 4 uL First strand buffer (Invitrogen)+2 uL DTT (Invitrogen)+1 uL RNAse OUT (Invitrogen)+0.5 uL SuperScript II (Invitrogen) was added to each sample and then incubated at RT for 10 minutes, followed by 42° C. for 50 minutes and 70° C. for 15 minutes. cDNA from RT-PCR was diluted into a total volume of 500 uL of RNAse free water. 5 uL of cDNA per reaction was combined with 7.5 uL Cyber-Green Sensi mix (Bioline), 0.6 uL each of forward primer and reverse primers, and 1.3 uL of RNAse free water. PCR was performed using a Stratagene Thermocycler with using 1 cycle at 95° C. for 10 minutes, then 40 cycles of 95° C. for 30 seconds, 60° C. for 30 seconds and 72° C. for 30 seconds followed by 1 cycles at 95° C. for 1 minutes. A dissociation curve in the range of 55° C.-95° C. was produced at the conclusion of each Q-PCR run to confirm the presence of single amplification products. All Q-PCR data show the average of three experiments and error bars show standard error of the mean. hESCs (H9) were used a negative control in all the experiments and error bars represent standard error of the mean (SEM).

Immunostaining hPSCs or their differentiated progenitors were fixed for 20 minutes at 4° C. in 4% paraformaldehyde and then washed three times in PBS. Cells were incubated for 20 minutes at room temperature in PBST (0.1% Triton X100; Sigma; in PBS) containing 10% donkey serum (Serotec Ltd.) and subsequently incubated overnight at 4° C. with primary antibody (Table 11) diluted in 1% donkey serum in PBST. Cells were then washed three times in PBS and incubated with secondary antibodies in 1% donkey serum in PBST for 2 hours at room temperature. Unbound secondary antibody was removed by three 5 minutes washes in PBS. Hoechst 33258 was added to the first wash (Sigma-Aldrich; 1:10, 000).

3D organoids were removed from Matrigel, fixed in 4% paraformaldehyde and embedded in 4% agarose, before processing for paraffin sections. Following antigen retrieval, samples were permeabilised with 0.5% Triton X-100 and blocked in 10% FBS before overnight incubation in primary antibody. Samples were washed with PBS and incubated with secondary antibodies for 1 hour at room temperature, before being counter-stained using DAPI. Samples were imaged using a Zeiss Imager M.2, equipped with AxioCam MRm and MRc cameras and AxioVision software for image capture.

Flow Cytometry

Adherent cells were washed twice in PBS and then incubated for 20 minutes at 37° C. in cell dissociation buffer (Invitrogen, Carlsbad, Calif., http://www.invitrogen.com). Cells were dissociated by gentle pipetting and resuspended at approximately 0.1-1×10° cells per milliliter in PBS. Cells were pelleted and fixed by resuspending cells in 4% paraformaldehyde solution at 4° C. for 20 minutes. Cells were washed in PBS and then blocked in PBS+10% normal donkey serum (NDS) containing 0.1% azide (Serotec Ltd., Oxford, U.K.). To permeabalise cells, pelleted cell were resuspended in 2 mL of SAP buffer (0.1% (w/v) saponin In Hanks' Balanced Salt Solution). Cells were then incubated in a solution of 0.1% SAP 1% Donkey serum+the primary antibody and incubated for at least 2 hours at room temperature or overnight at 4° C. Cells were then washed three times in PBS+1% NDS and incubated with secondary antibodies in SAP buffer for 2 hours at room temperature or 4° C. overnight. Unbound secondary antibody was removed by three washes in PBS. Cells were then analyzed using a FACS Calibur machine (BD Biosciences, San Jose, Calif., USA). Number of positive cells was recorded as the average from three separate experiments.

Generation of hIPSCs hIPSCs (BBHX8 and A1TATD) were derived using retrovirus mediated reprogramming of human skin fibroblasts using the Yamanaka factors as described [7].

Generation of GFP hPSCs and Clonal Analyses

GFP expressing H9, BBHX8 and A1ATD-1 were generated by stable transfection using lipofectamine 2000 (Invitrogen) as described previously[19]. GFP positive cells were differentiated into foregut cells and then dissociated into single cells. An individually isolated GFP cell was then transferred into a well containing non-GFP positive hFSCs. Wells were visually inspected 12 hrs after plating and wells containing a single GFP-positive hFSC were selected for clonal expansion.

Enzyme Linked Immunosorbent Assay (ELISA)

hESCs grown for 25 days in culture conditions inductive for pancreatic specification were cultured in differentiation medium without insulin for 24 h prior to Glucose stimulation. Cells were washed three times with PBS and pre-incubated in DMEM supplemented with 2.2 mM glucose (Invitrogen) for 60 min at 37° C. Pre-incubated cells were grown in DMEM containing 22 mM glucose or alternatively 2.2 mM glucose for 15 or 60 minutes. Supernatants were collected for determination of C-peptide release. ELISA analyses were performed using the Mercodia Ultrasensitive C-peptide ELISA kit (Mercodia). Concerning Abumin and ATT secretion assays, High binding surface COSTAR 96-well plates (Corning, N.Y., USA) were coated overnight with affinity-purified rabbit polyclonal antibodies against $\alpha_1$-antitrypsin (Abcam 31657, Cambridge, UK) and Albumin (Abcam 87564, Cambridge, UK) at 2 µg/ml in carbonate/bicarbonate buffer (Na2CO3/NAHCO3, pH 9.5). After washing (0.9% w/v NaCl, 0.05% v/v Tween 20), the plates were blocked for two hours in blocking buffer (PBS, 0.25% w/v BSA, 0.05% v/v Tween 20). Culture medium were diluted in blocking buffer and 50 µl added to each well then incubated for two hours. After washing, the wells were incubated with corresponding monoclonal antibodies (1 µg/ml diluted in blocking buffer), and incubated for two hours. Bound monoclonal antibodies were detected with rabbit anti-mouse IgG HRP-labelled antibody (Sigma Aldrich, Haverhill, UK, 1:20,000) for one hour. The reaction was developed with TMB liquid substrate (Sigma Aldrich, Haverhill, UK) for 10 minutes in the dark and the reaction was stopped with 1 M $H_2SO4$. Absorbance was read at 450 nm on a Thermo-max microplate reader (Molecular Devices, Sunnyvale, Calif., U.S.A.).

Cytochrome P450 Activity

Cyp3A4 activity assay was measured in triplicate using the P450-Glo assay kit (Promega) according to the manufacturer's instructions. Cytochrome activity was then analysed using a P450-GloMax 96 microplate luminometer.

Periodic Acid Schiff (PAS) Staining

PAS staining was carried out on cells in triplicate using a kit (Sigma 395B-1KT) under the guidance of manufacturer's instructions. Diastase digestion was subsequently performed to confirm the positive staining was due to presence of Glycogen.

Uptake of LDL

The Dil-LDL staining kit was purchased from (Cayman Chemicals, MA) and the assay was performed according to the manufacturer's instructions.

Results

We previously developed a defined culture system to direct the differentiation of hPSCs into a near homogenous population of Definitive Endoderm (DE) cells which have the capacity to differentiate into hepatocytes and pancreatic progenitors [4-9]. Cells grown in these culture conditions successively express primitive streak markers (T, Eomes, Mixl1), down regulate pluripotency markers (NANOG, SOX2 and POU5F1) and progressively up regulate definitive endoderm marker (CXCR4, CERB and SOX17). Flow cytometric analyses showed that 80% of the resulting DE population co-express CXCR4 and Sox17. Interestingly, the resulting population of DE cells is negative for genes marking the foregut (SOX2), the midgut/hindgut (CDX2), the pancreas (PDX1, PTF1a), the liver (AFP), and the lungs (Nkx2.1, TBX1). This confirms that DE cells generated in vitro correspond to early endoderm progenitor cells prior to antero-posterior patterning or organogenesis.

We next examined the capacity of DE cells to differentiate into representatives of the anterior and posterior domains of the primitive gut tube. We screened various growth factors and found that Activin-A blocks CDX2 expression while inducing expression of anterior gut markers such as SOX2, HHEX, and HOXA3. On the other hand, DE cells grown in the presence of the GSK3β inhibitor CHIR99021 express midgut/hindgut markers such as CDX2, and HOXC5 and show no expression of anterior markers. During both Activin-A treatment and CHIR treatment cells express high levels of the primitive gut markers GATA4, HNF4a, EpCAM and HOXA2 demonstrating that under these conditions, cells retain their endodermal identity. Of note, flow cytometric analyses revealed that 90% of the cells express SOX2 after Activin-A treatment while 85% of the cells were positive for CDX2 after CHIR99021 treatment. Similar results were obtained using two hIPSC lines (BBHX8, A1ATD.1). Taken together, these data show that Activin-A and GSK3beta signalling direct the antero-posterior patterning of human DE in vitro.

To further validate the identity of the cells generated in the presence of Activin-A or CHIR99021, we decided to test their capacity to differentiate into intestinal cells. SOX2$^+$ cells and CDX2$^+$ cells were grown into three dimensional organoid culture conditions[10] known to promote posterior gut differentiation. Sox2$^+$ cells grown under these conditions ceased to proliferate and could not be expanded whereas CDX2$^+$ cells formed spheroids with highly folded structures resembling intestinal epithelium and expressed intestinal markers (Mucin, Villin and Chromagranin A). Furthermore, these organoids could be expanded for at least 2 months while displaying a progressive increase in the markers of adult intestinal epithelium. Finally, comparative immunostaining analysis of CDX2+cells derived organoids with primary mouse intestinal organoids demonstrated a polarised epithelium with apical Villin expression in both types of organoids. These data confirm that CDX2$^+$ cells generated in the presence of CHIR99021 have differentiation potential to form Midgut/hindgut progenitors while Activin-A induced SOX2$^+$ have lost this capacity. These SOX2$^+$ cells could consequently be equivalent to foregut progenitors [11].

Figure 1B:
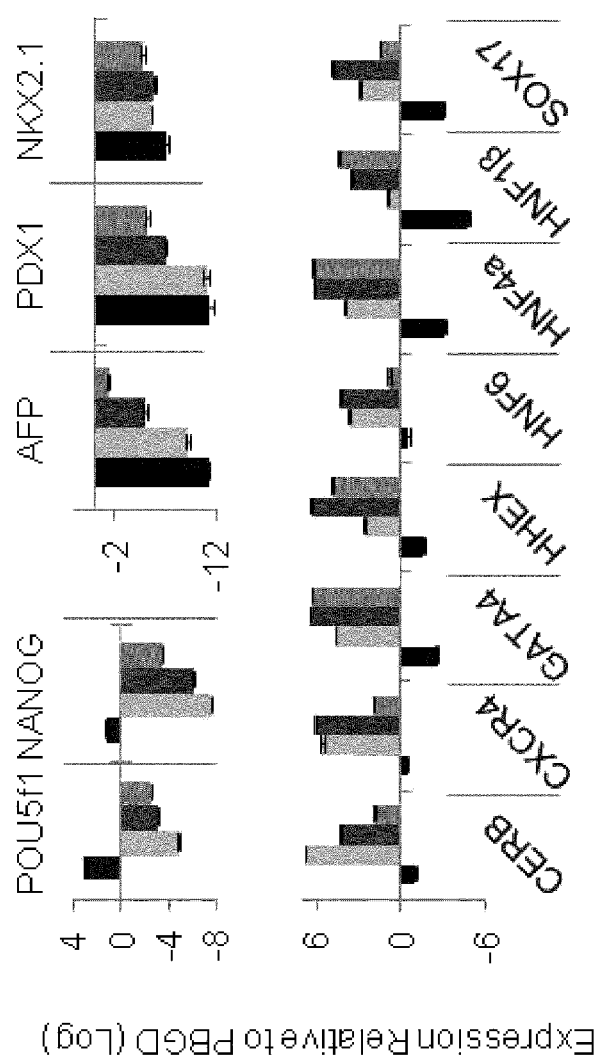
FIGS. 1B and 1C show Q-PCR and Immunostaining analyses showing that hFSCs derived from hESCs (H9) and hIPSCs (BBHX8, A1ATD-1) can be grown for up to 10 passages while maintaining the expression of foregut markers (CERB, HNF1β, HNF6, CXCR4, GATA4, HHEX, HNF4α, SOX17). The expression of pluripotency (POU5F1, NANOG), pancreatic (PDX1), hepatic (AFP) and lung (NKX2.1), gut (CDX2) was not observed during propagation.
Figure 1C:
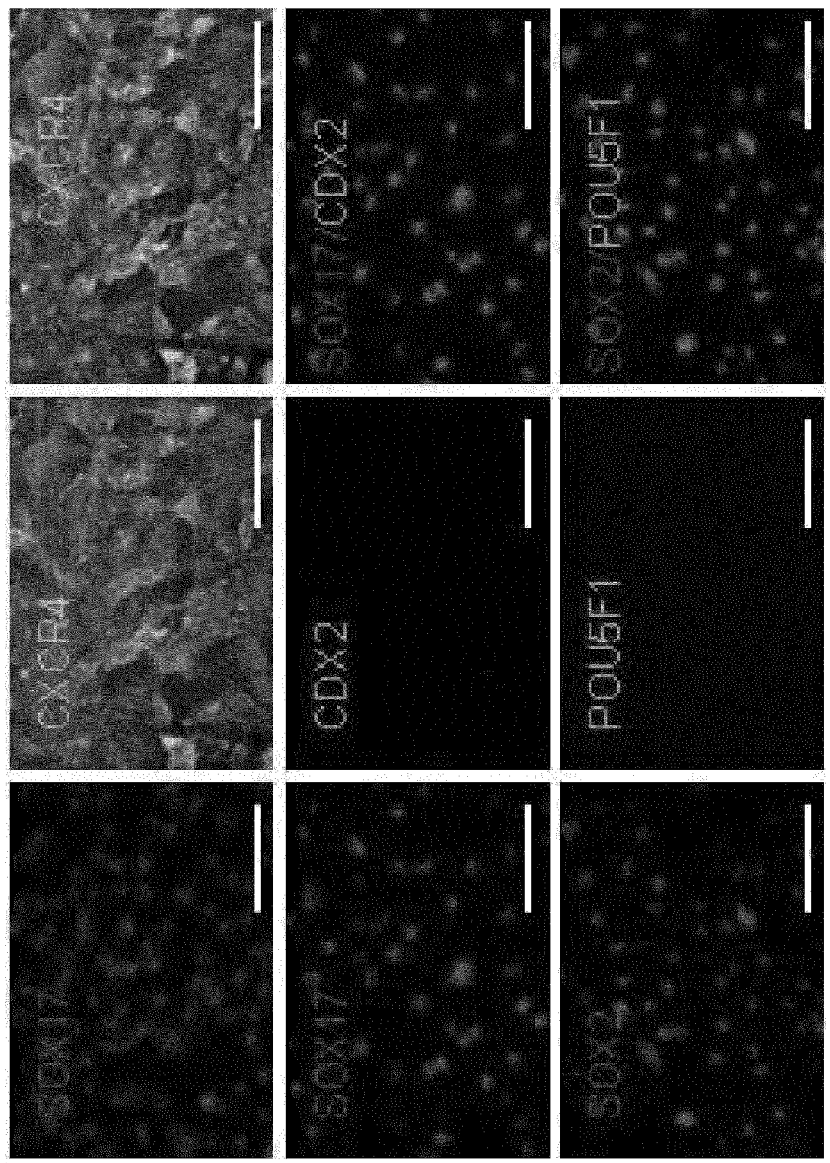
Figure 1D:
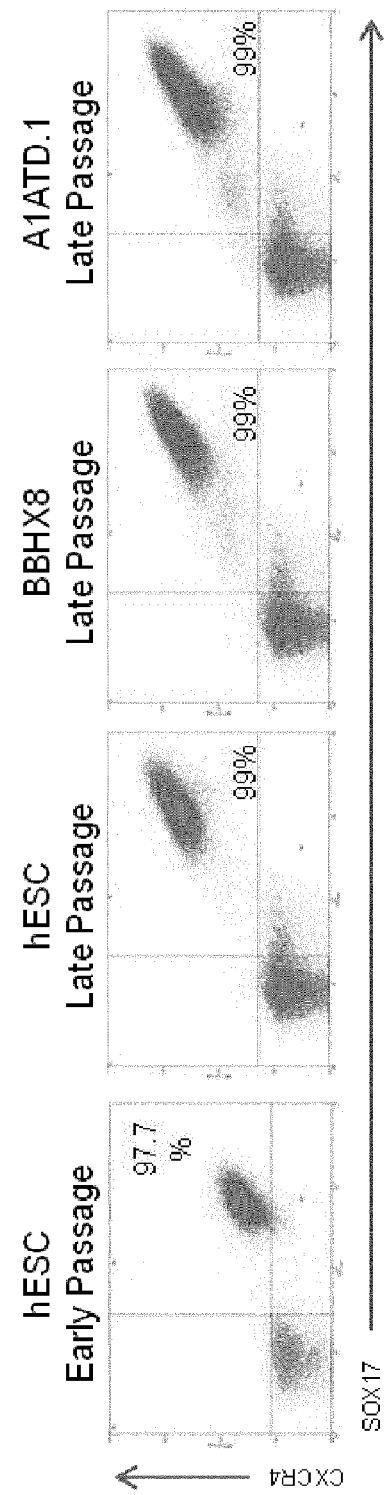
FIG. 1D shows that a near homogenous population of hFSCs co-expressing SOX17/CXCR4 was evident after passage 3 and was stable in culture beyond passage 6 as shown by FACS analyses. Grey population represents secondary antibody only control.

We then tested the capacity of foregut SOX2+ cells to self-renew in vitro. DE cells derived from hESCs were differentiated for 4 days in the presence of Activin-A and were subsequently cultured in the presence of a diverse combination of growth factors. Following this approach, we identified that the combination of Activin-A, bFGF, BMP4, HGF, EGF and heparin was sufficient to expand Foregut SOX2+ cells for more than 10 passages at a ratio of 1:4-1:6 (FIG. 1A). Culture conditions optimal for expansion of foregut cells produced little cell death or differentiation in the foregut cells themselves, however significant cell death of contaminating cells such as neuronal-like and fibroblast-like cells was observed which served only to enhance the foregut cultures over time. After 5 passages in these culture conditions, foregut SOX2+ cells did not express pluripotency (POU5f1 and NANOG), lung (NKX2.1), hepatic (AFP), or pancreatic (PDX1) markers while maintaining the expression of foregut markers (HNF4α, SOX17, CXCR4, EpCAM, HNF1β, GATA4, Cer, SOX2. HNF6, and HNF1beta; FIGS. 1B-C). Flow cytometric analyses showed that SOX17 and CXCR4 were co-expressed near homogenously (FIG. 1D). Importantly, similar results were obtained with 2 hIPSC lines (BBHX8, A1ATD.1) [5-7]. Together, these data demonstrate that our culture system captures a homogenous population of foregut cells which can self-renew in vitro and thus could represent a new type of endodermal stem cell (referred thereafter as human Foregut Stem Cells or hFSCs).

Figure 2A:
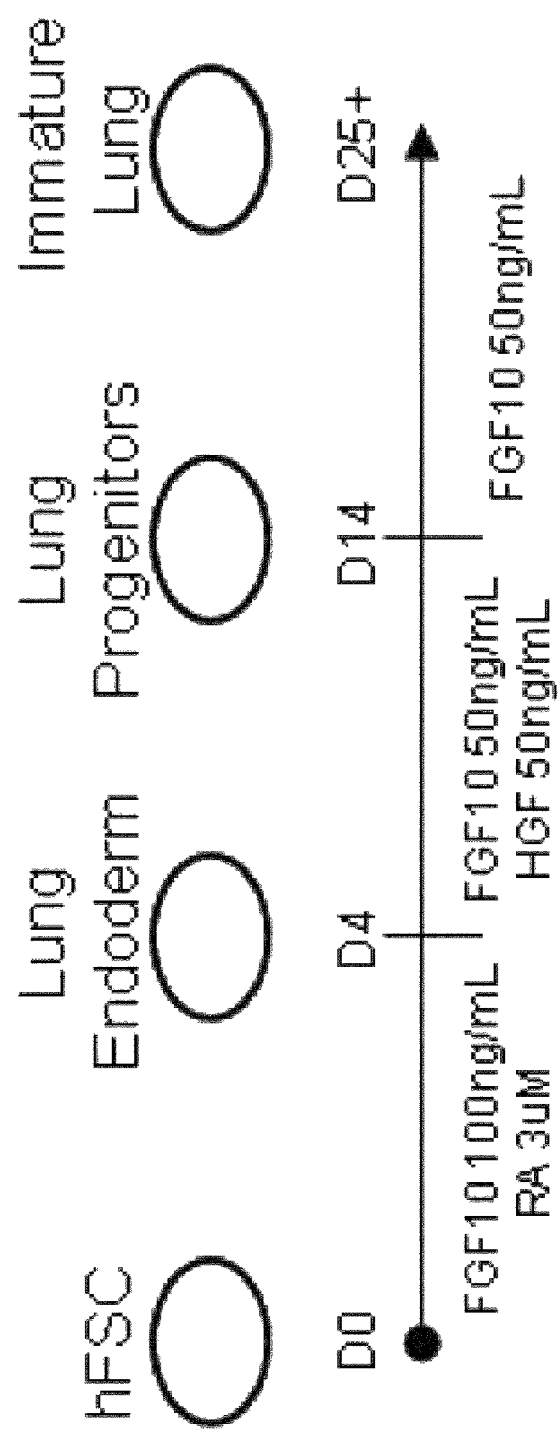
FIG. 2A shows an example of a method to differentiate hFSCs into lung cells.
Figure 2B:
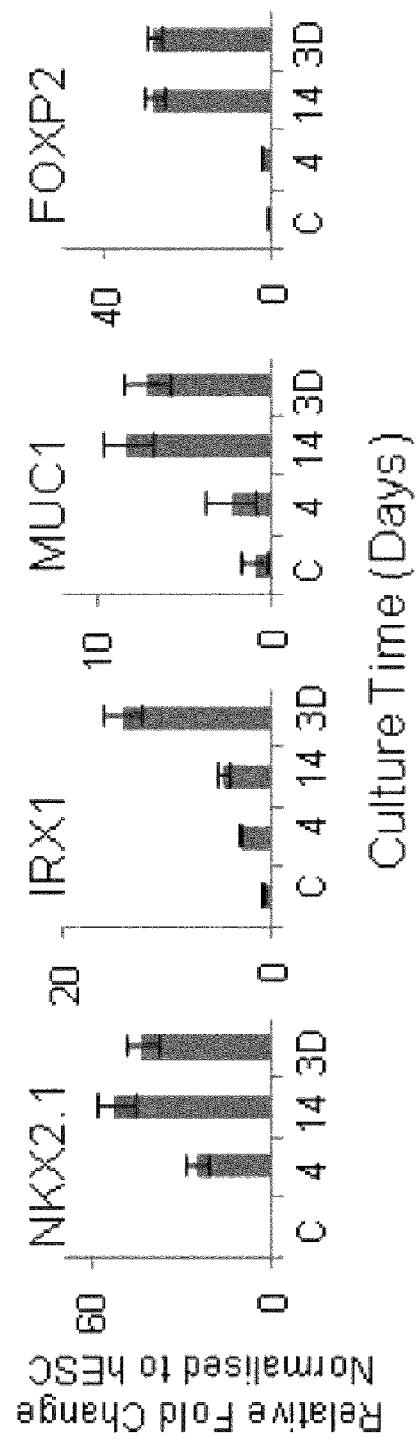
FIG. 2B shows Q-PCR results indicating that, under these conditions, hFSCs upregulate early lung endoderm markers (NKX2.1, FOXP2, IRX1) as well as more mature markers (MUC1) as shown by Q-PCR.
Figure 2C:
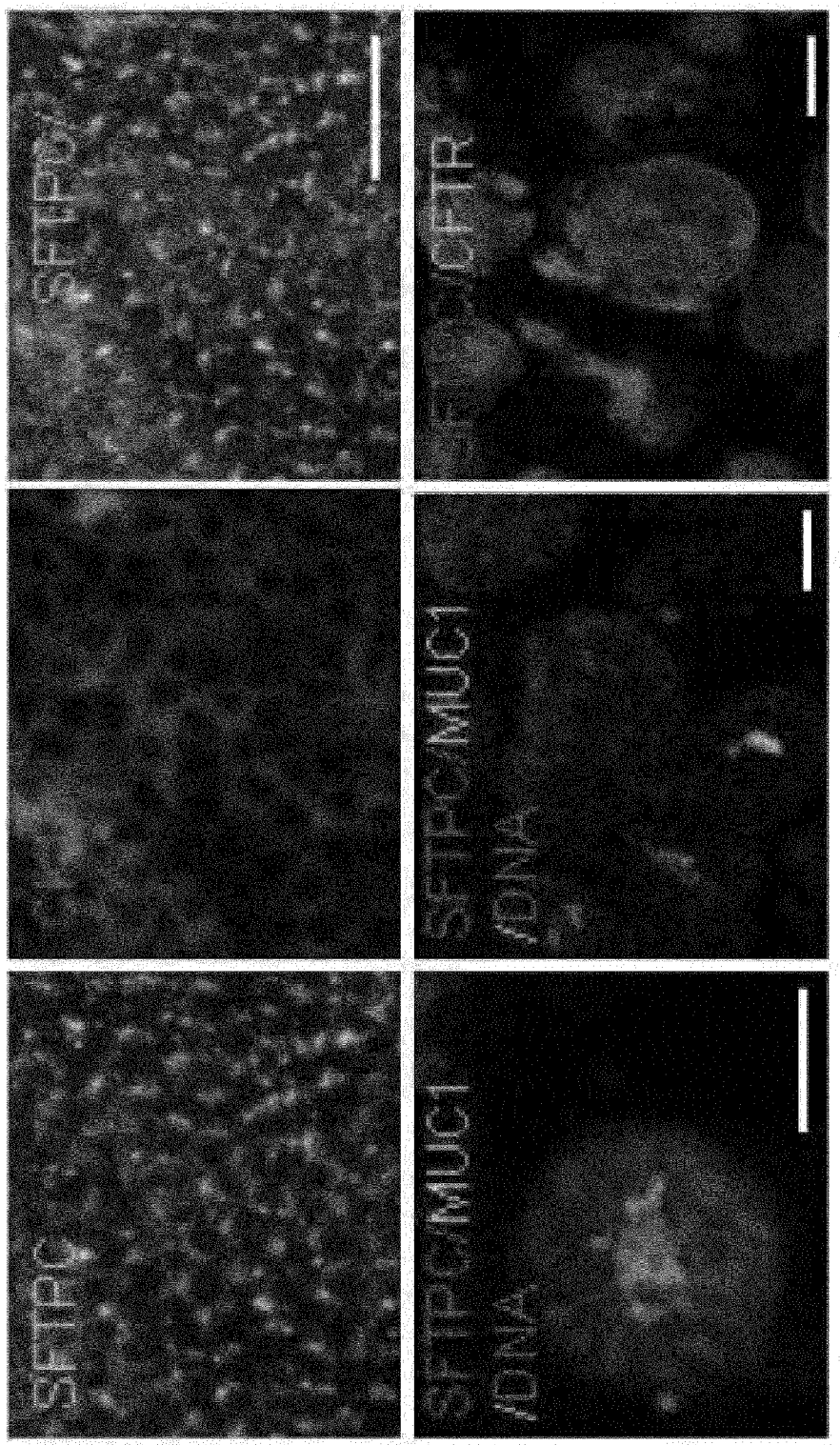
FIG. 2C shows that the resulting cells grown in 3D culture generate branched and cystic structured cell aggregates expressing distal airway markers (SFTPC, MUC1, CK18).
Figure 2D:
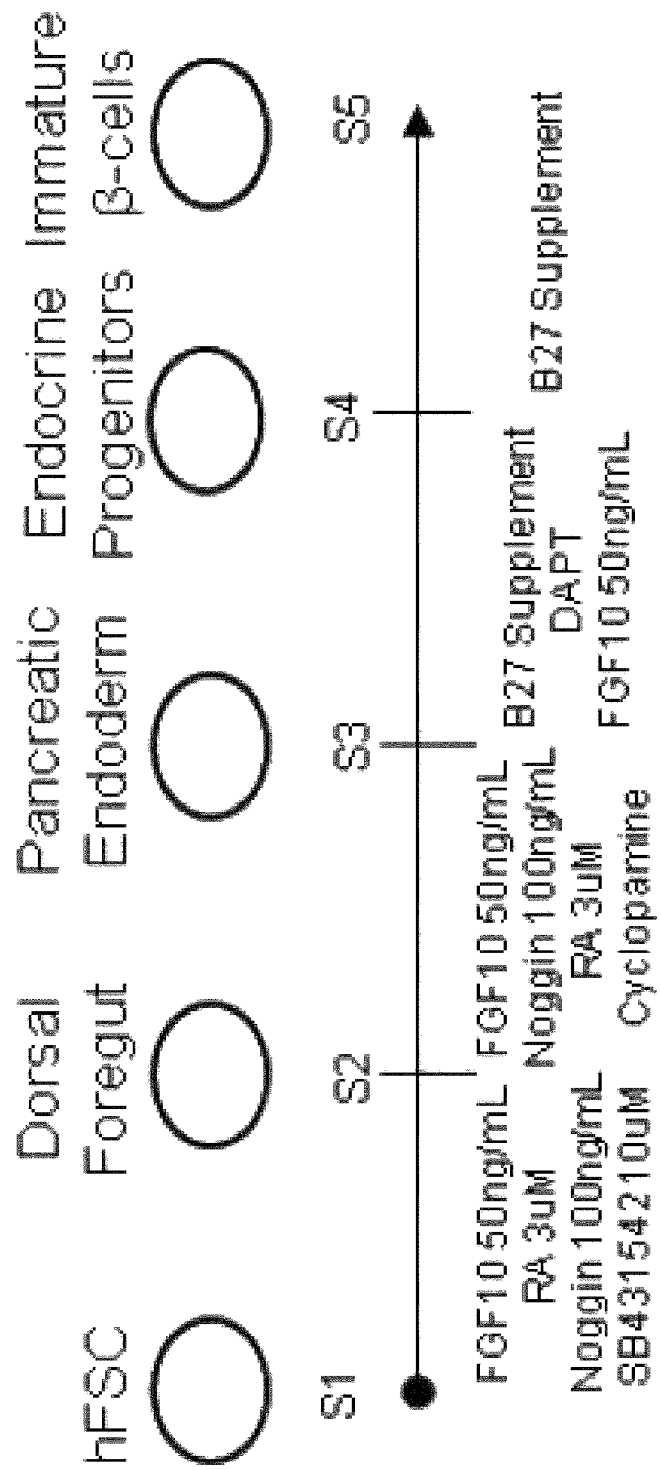
FIG. 2D shows an example of a method to differentiate hFSCs into pancreatic cells.
Figure 2E:
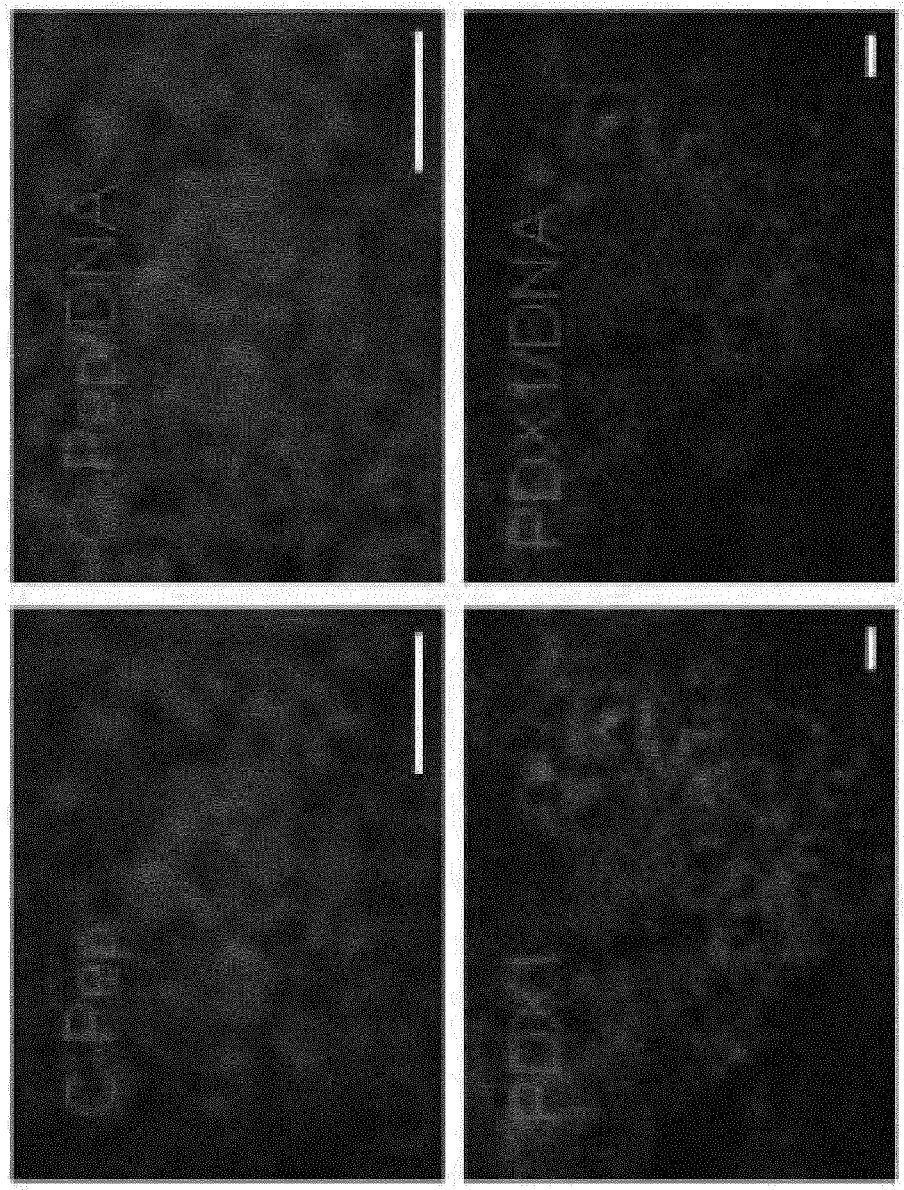
FIG. 2E shows that hFSCs grown in these culture conditions progressively express pancreatic bud markers (PDX1, HLXB9) and then endocrine markers (INS, NGN3).
Figure 2H:
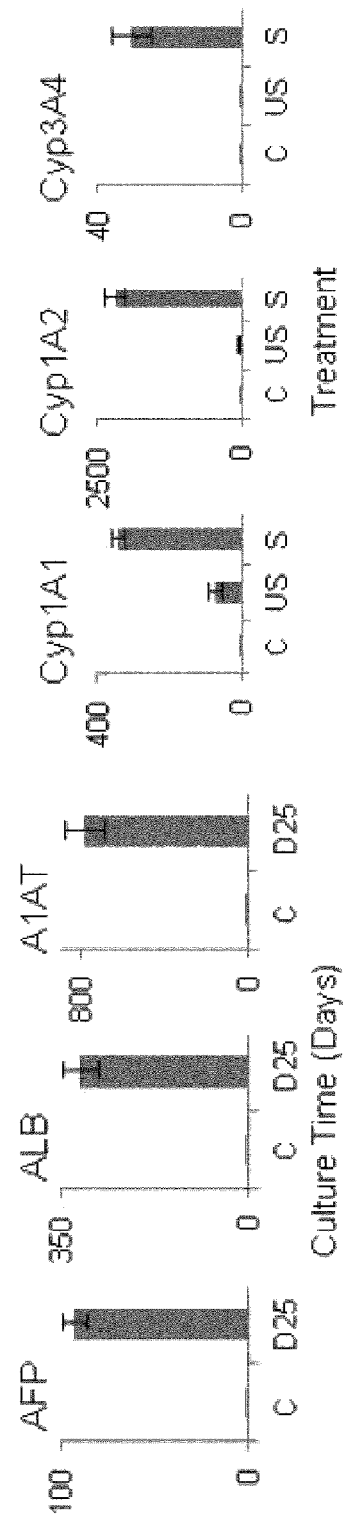
FIG. 2h shows that, after 25 days of differentiation, cells expressed hepatic markers (ALB, AFP, A1AT) and displayed inducible cytochrome P450 activity (C=HESC, US=unstimulated, S-stimulated).
Figure 2I:
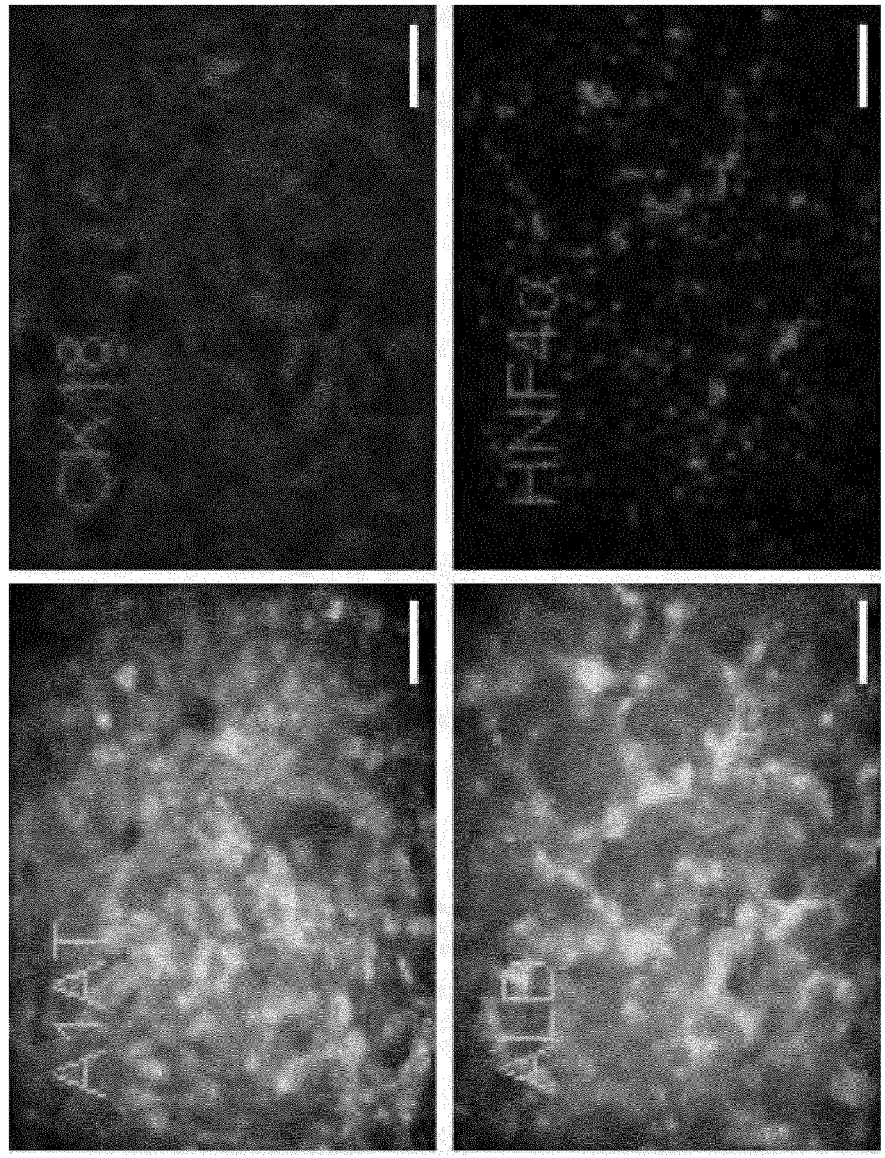
FIG. 2I shows immunostaining results which confirm that the cells express mature hepatocyte markers (ALB, A1AT, CK18, HNF4α).

To confirm this hypothesis, we tested the ability of hFSCs to differentiate into lung, liver and pancreatic cells. hFSCs grown in culture conditions inductive for lung differentiation (FIG. 2A) up regulated early pulmonary endoderm markers (Nkx2.1, FOXP2 and IRX1, FIG. 2B). Furthermore, cells differentiated in 3D conditions formed aggregates with both branched cystic structures resembling distal airway epithelium as well as large single cyst-aggregates more representative of Type II pneumocytes. Approximately 70% of cells expressed the early pulmonary endoderm marker NKX2.1, accordingly, Q-PCR and immunostaining analyses confirmed the expression of both lung type II alveoli cell markers (NKX2.1, ABCA3, MUC1) and distal airway markers (NKX2.1, CK18, CFTR, SFTPC, GATA6, FIG. 2B-C). hFSCs were also grown in culture conditions inductive for pancreatic specification[4] (FIG. 2D) leading to the sequential expression of early pancreatic markers (HLXB9, PDX1), then endocrine progenitor marker (Ngn3) and finally beta cell marker (Insulin) (FIG. 2E). As reported previously approximately more than 80% of cells were PDX1 positive at stage 4 of the pancreatic differentiation protocol [4]. After 18 days of differentiation, c-peptide, PDX1 and somatostatin expressing cells could be detected by immunostaining and c-peptide release was detected upon glucose stimulation (FIG. 2F). Finally, hFSCs grown in culture conditions inductive for hepatic specification [7, 9] (FIG. 2G) expressed liver markers (AFP, ALB, A1AT, CYP1A1, CYP1A2, CYP1A4) display inducible cytochrome activity (FIGS. 2H and 2I), secrete AAT and Albumin, and take up cholesterol and Cariogreen. Hepatic-like cells generated from hFSCs were more than 90% double positive for the hepatic markers albumin and alpha-1-antitrypsin as reported previously [7,9] Importantly, multiple hFSC lines derived from different hIPSC lines displayed similar differentiation efficiency. Taken together, these data demonstrate that hFSCs have the capacity to differentiate into foregut derivatives including lung, pancreatic and hepatic cells thereby confirming that they are multipotent.

To further reinforce these results, we decided to confirm that single hFSC are multipotent. hFSCs grow as an epithelium and single cell isolation systematically resulted in cell death. To by-pass this limitation, we generated GFP expressing hFSCs which were dissociated into single cells and individually placed on a well of a 24 wells plate containing non GFP expressing hFSCs. The following day, wells containing a single GFP-positive hFSCs were marked for expansion and after 5 passages, the resulting cells were differentiated into pulmonary, hepatic and pancreatic cells. hFSCs GFP positive cells grown in these respective culture conditions expressed pulmonary (Pro-SFTPC and MUC1), hepatic (ALB, A1AT, AFP and HNF4a and LDL up take), and pancreatic (PDX1, INS, NGN2 and SST) markers thereby providing the necessary evidence that hFSCs generated from hESCs and hIPSCs are multipotent stem cells.

Figure 3A:
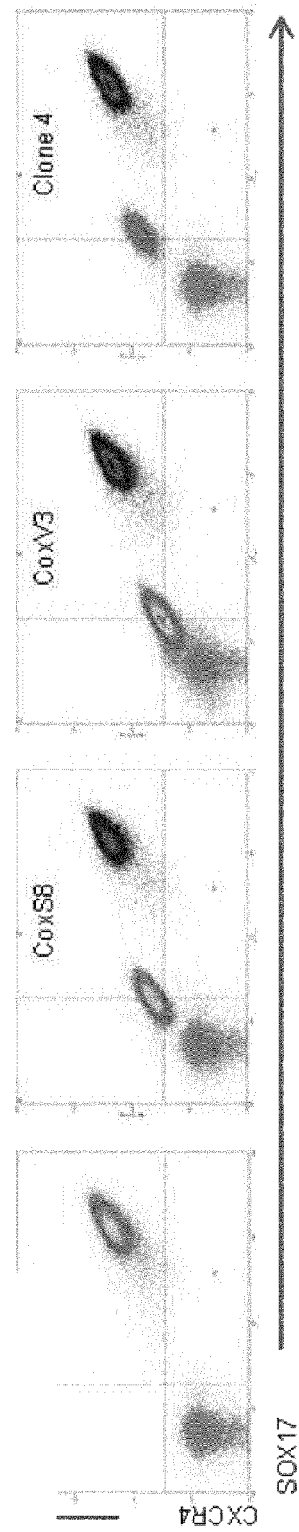
FIG. 3A shows FACS analyses indicating the fraction of cells co-expressing the endoderm/foregut markers SOX17/CXCR4 before isolation (coloured plot) and after expansion (passage 5, Black plot) of hFSCs generated from hIPSC lines with high (BBHX8) and low (CS8, CV3 and Cl4) endoderm differentiation capacity. Gates were set to secondary antibody only controls, grey population.
Figure 3B:
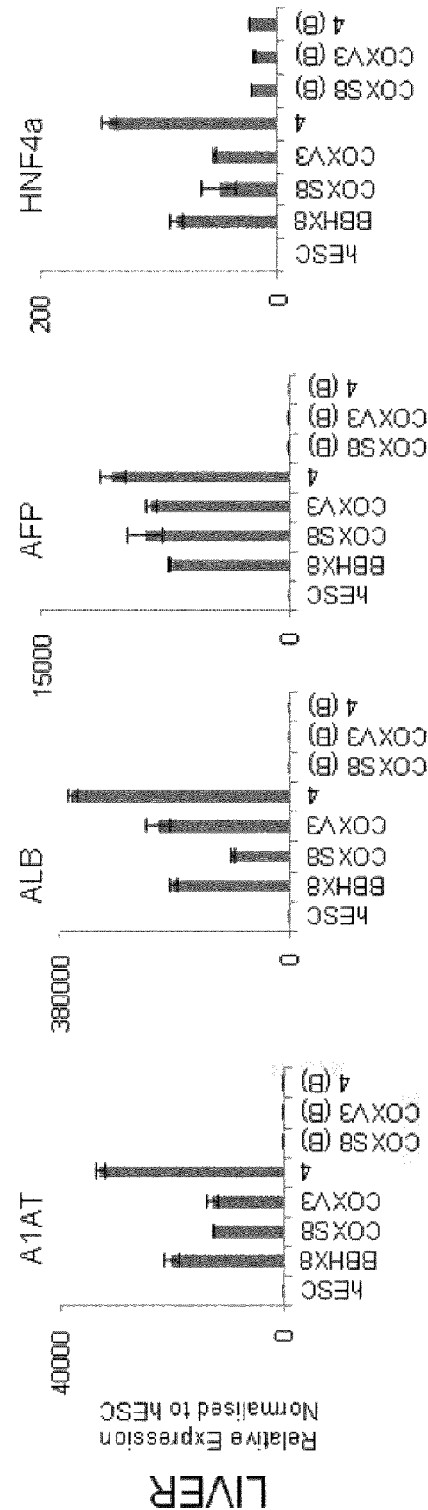
FIGS. 3B and 3C show that hIPSCs with low endoderm capacity of differentiation cannot differentiate into liver or pancreatic cells (COXS8(B), COXV3 (B), 4(B)) while hFSCs generated from the same cells lines and split 5 times can differentiate into cells expressing markers for hepatocytes (A1AT, AFP, ALB HNF4a) and pancreatic cells (GCG, PDX1, INS, NGN3) at levels comparable to positive control (BBHX8).
Figure 3C:
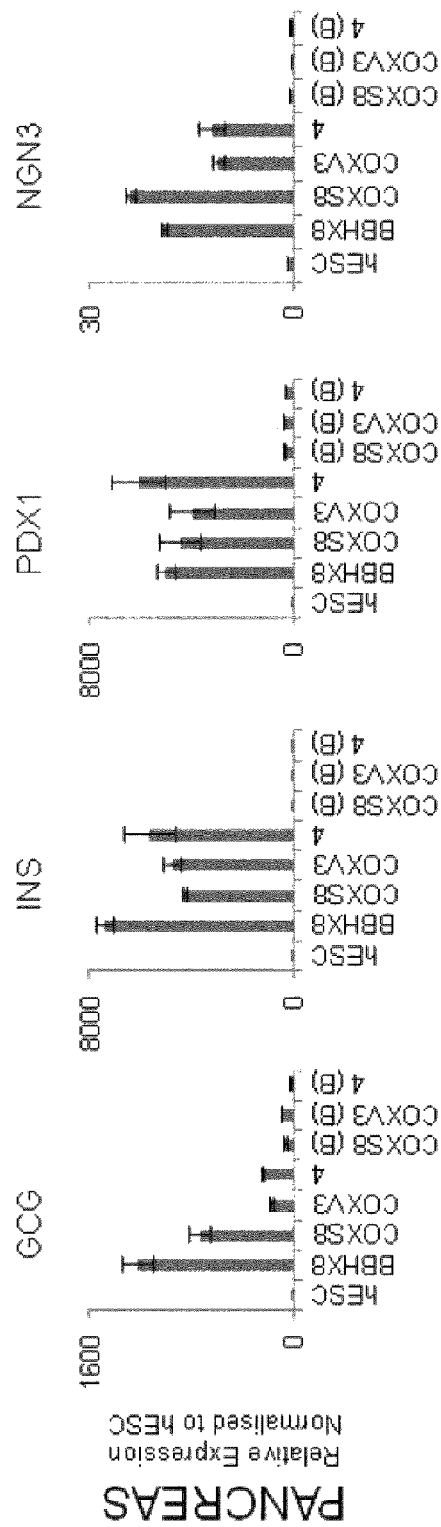

From a panel of 48 hIPSC lines derived from 16 individuals we identified at least 3 lines that are unable to differentiate into homogeneous populations of DE. These endoderm resistant hIPSC lines (COXS8, COXV3 and Line4) produced less than 30% of SOX17 DE cells (FIG. 3A). Nevertheless, this heterogeneous population could be grown for 3 additional days in the presence of Activin-A to promote foregut specification and the resulting cells were transferred into culture conditions supporting hFSCs expansion. Interestingly, contaminating cells of non-endodermal origin stopped proliferating and progressively disappeared upon passaging. Flow cytometric analyses show that cells grown for 5 passages expressed homogenously SOX17 and CXCR4 (99%) similarly to hFSCs generated from hIPSCs proficient for endoderm production (FIG. 3A). Therefore, our culture system selectively amplifies hFSCs even when they originate from a heterogeneous population of DE cells. The resulting population of hFSCs was expanded for 2 additional passages and then transferred into culture conditions inductive for pancreas and liver differentiation. Cells differentiated toward the liver lineage expressed hepatic markers (AAT, ALB, AFP, HNF4) at a level similar to hepatocyte-like cells generated from control hFSCs (FIG. 3B). Similarly, cells differentiated towards the pancreatic lineage cells expressed PDX1, INS and NGN3 (FIG. 3C). Together, these results show that hFSCs can be easily generated from hIPSCs with reduced endoderm differentiation capacity for the production of hepatic and pancreatic cells. Therefore, derivation of hFSCs can be easily achieved numerous hIPSC lines and will allow the production of cells with clinical interests from a broad diversity of patients.

Our results describe a stepwise method to differentiate hPSCs into a multipotent population of foregut stem cells (FIG. 4).

Importantly, production of foregut cells has been reported previously [12], however, our study provides for the first time a culture system allowing the isolation, expansion and differentiation of multipotent self-renewing Foregut Stem Cells. Similarly, a recent study has shown that multipotent DE cells could be expanded in vitro [3, 13], yet these cells express a broad diversity of markers which render their embryonic identity difficult to establish. Furthermore, they can only be generated using feeders, Matrigel, 3 dimensional culture conditions and serum, all of which are not compatible with large scale or clinical applications. Our culture system addresses several of these limitations, while hFSCs share fundamental characteristics with their in vivo counterpart. Nevertheless, the exact type of foregut cell described here is yet to be fully defined as lineage tracing experiments have shown that foregut may contain only bipotential progenitors able to differentiate toward the hepatic and pancreatic lineages [14]. However, the property of in vivo progenitors is likely to be dictated by their localisation within the foregut and thus their surrounding environment. Moreover, the gut tube initially possesses a high degree of plasticity. Indeed, the hindgut domain if taken at an early time point is capable of producing liver and pancreatic bud structures when either juxtaposed against foregut cardiac mesoderm or placed in culture conditions with BMP and FGF [15, 16]. This suggests that during the early stages of gut formation the entire gut epithelial sheet could be multipotent. Thus, the culture system described here could be less restrictive enabling hFSCs to display the full range of their developmental plasticity.

Finally, expansion of a multipotent foregut progenitor population is of considerable interest with regard to clinical applications. Indeed, our culture system is compatible with large scale production of a near homogenous population of endodermal cells which could greatly simplify the production of cells for cell based therapy. Furthermore, derivation of hFSCs allowed for differentiation of all the tested hIPSC lines without the need to establish individual protocols. Therefore, hFSCs not only provide a unique in vitro model of human development but also represent an important tool to deliver the clinical promises of hIPSCs in the field of personalised medicine.

REFERENCES

1. Lund, R. J. et al Nat Rev Genet. 13(10): p. 732-44.
2. Falk, A., et al. PLoS One. 7(1): p. e29597.
3. Sneddon, J. B. et al Nature.
4. Cho, C. H., et al. Diabetologia.
5. Brown, S., et al. Stem Cells. 29(8): p. 1176-85.
6. Vallier, L., et al Stem Cells, 2009. 27(11): p. 2655-66.
7. Rashid, S. T., et al J Clin Invest. 120(9): p. 3127-36.
8. Touboul, T., et al. Hepatology. 51(5): p. 1754-65.
9. Yusa, K., et al Nature. 478(7369): p. 391-4.
10. Spence, J. R., et al. Nature. 470(7332): p. 105-9.
11. Arnold, K., et al. Cell Stem Cell. 9(4): p. 317-29.
12. Green, M. D., et al. Nat Biotechnol. 29(3): p. 267-72.
13. Cheng, X., et al. Cell Stem Cell. 10(4): p. 371-84.
14. Deutsch, G., et al. Development, 2001. 128(6): p. 871-81.
15. Bossard, P. et al Development, 2000. 127(22): p. 4915-23.
16. Wells, J. M. et al Development, 2000. 127(8): p. 1563-72.
17. Teo, A. K., et al Genes Dev. 25(3): p. 238-50.
18. Vallier, L., et al PLoS One, 2009. 4(6): p. e6082.
19. Vallier, L., et al Proc Natl Acad Sci USA, 2001. 98(5): p. 2467-72.
20. PCT/EP2013/069188
21. Kim et al Nature 2010 467 285-290

TABLE 1

| (RPMI-1640 medium) | | |
|---|---|---|
| COMPONENT | g/L | g/L |
| INORGANIC SALTS | | |
| $Ca(NO_3)_2 \cdot 4H_2O$ | 0.1 | 0.1 |
| $MgSO_4$ (anhyd) | 0.04884 | 0.04884 |
| KCl | 0.4 | 0.4 |
| $NaHCO_3$ | — | 2.0 |
| NaCl | 6.0 | 6.0 |
| $Na_2HPO_4$ (Anhyd) | 0.8 | 0.8 |

TABLE 1-continued

| (RPMI-1640 medium) | | |
|---|---|---|
| COMPONENT | g/L | g/L |
| AMINO ACIDS | | |
| L-Arginine (free base) | 0.2 | 0.2 |
| L-Asparagine (anhyd) | 0.05 | 0.05 |
| L-Aspartic Acid | 0.02 | 0.02 |
| L-Cystine•2HCl | 0.0652 | 0.0652 |
| L-Glutamic Acid | 0.02 | 0.02 |
| L-Glutamine | 0.3 | 0.3 |
| Glycine | 0.01 | 0.01 |
| L-Histidine (free base) | 0.015 | 0.015 |
| Hydroxy-L-Proline | 0.02 | 0.02 |
| L-Isoleucine | 0.05 | 0.05 |
| L-Leucine | 0.05 | 0.05 |
| L-Lysine•HCl | 0.04 | 0.04 |
| L-Methionine | 0.015 | 0.015 |
| L-Phenylalanine | 0.015 | 0.015 |
| L-Proline | 0.02 | 0.02 |
| L-Serine | 0.03 | 0.03 |
| L-Threonine | 0.02 | 0.02 |
| L-Tryptophan | 0.005 | 0.005 |
| L-Tyrosine•2Na•2$H_2O$ | 0.02883 | 0.02883 |
| L-Valine | 0.02 | 0.02 |
| VITAMINS | | |
| D-Biotin | 0.0002 | 0.0002 |
| Choline Chloride | 0.003 | 0.003 |
| Folic Acid | 0.001 | 0.001 |
| myo-Inositol | 0.035 | 0.035 |
| Niacinamide | 0.001 | 0.001 |
| p-Amino Benzoic Acid | 0.001 | 0.001 |
| D-Pantothenic Acid•½Ca | 0.00025 | 0.00025 |
| Pyridoxine•HCl | 0.001 | 0.001 |
| Riboflavin | 0.0002 | 0.0002 |
| Thiamine•HCl | 0.001 | 0.001 |
| Vitamin B-12 | 0.000005 | 0.000005 |
| OTHER | | |
| D-Glucose | 2.0 | 2.0 |
| Glutathione (reduced) | 0.001 | 0.001 |
| HEPES | — | — |
| Phenol Red•Na | 0.0053 | 0.0053 |
| ADD | | |
| $NaHCO_3$ | 2.0 | — |

The invention claimed is:

1. A method for producing a population of foregut stem cells (FSCs) comprising:
    i) providing a population of definitive endoderm cells (DECs), and
    ii) culturing the DECs in a foregut induction medium consisting of a chemically defined nutrient medium supplemented with a TGFβ ligand to produce a population of foregut stem cells (FSCs).

2. The method according to claim 1 wherein the population of DECs is produced by a method comprising:
    i) culturing a population of pluripotent cells (PSCs) in a definitive endoderm (DE) induction medium comprising a TGFβ ligand, fibroblast growth factor (FGF), bone morphogenetic protein (BMP) and a PI3K inhibitor, and
    ii) allowing the PSCs to differentiate into DECs.

3. The method according to claim 2 wherein the pluripotent cells are human pluripotent cells.

4. The method according to claim 2 wherein the pluripotent cells are IPSCs.

5. The method according to claim 4 wherein the iPSCs are derived from antecedent cells obtained from an individual.

6. The method according to claim 2 wherein the pluripotent cells express one or more of the following pluripotency associated markers: Oct4, Sox2, Alkaline Phosphatase, POU5f1, SSEA-3, Nanog, SSEA-4, Tra-1-60, KLF-4 and c-myc.

7. The method according to claim 2 wherein the DE induction medium consists of a chemically defined nutrient medium supplemented with a TGFβ ligand, fibroblast growth factor (FGF), bone morphogenetic protein (BMP) and a PI3K inhibitor.

8. The method according to claim 2 wherein the TGFβ ligand is activin and/or the PI3K inhibitor is LY294002.

9. The method according to claim 1 wherein the population of DECs is a homogeneous population or a heterogeneous population.

10. The method according to claim 1 wherein the DECs express one or more of the following endoderm associated markers: Sox17, foxA2, Lhx1, CXCR4, GATA4, eomesodermin (EOMES), Mix11, HNF-3 beta, Cerberus, OTX4, goosecoid, C-kit, CD99, and Hex.

11. The method according to claim 1 wherein the TGFβ ligand is activin.

12. The method according to claim 1 wherein the FSCs express one or more of the following markers: SOX2, HHEX, HOXA3, HNF4α, SOX17, CXCR4, EpCAM, HNF1β, GATA4, Cer, and HNF6.

* * * * *